(12) United States Patent
Boppart et al.

(10) Patent No.: US 7,610,074 B2
(45) Date of Patent: Oct. 27, 2009

(54) MULTI-FUNCTIONAL PLASMON-RESONANT CONTRAST AGENTS FOR OPTICAL COHERENCE TOMOGRAPHY

(75) Inventors: Stephen A. Boppart, Champaign, IL (US); Alexander Wei, West Lafayette, IN (US)

(73) Assignees: The Board of Trustees of the University of Illinois, Urbana, IL (US); Purdue Research Foundation, West Lafayette, IN (US)

( * ) Notice: Subject to any disclaimer, the term of this patent is extended or adjusted under 35 U.S.C. 154(b) by 864 days.

(21) Appl. No.: 10/753,972

(22) Filed: Jan. 8, 2004

(65) Prior Publication Data

US 2005/0171433 A1 Aug. 4, 2005

(51) Int. Cl.
*A61B 5/05* (2006.01)
(52) U.S. Cl. .................. 600/407; 600/473; 600/476; 424/9.1; 424/9.6
(58) Field of Classification Search ............. 378/21, 378/62; 600/407, 420, 408, 425–429
See application file for complete search history.

(56) References Cited

U.S. PATENT DOCUMENTS

| | | | |
|---|---|---|---|
| 4,522,811 A | 6/1985 | Eppstein et al. |
| 5,095,487 A | 3/1992 | Meyerhofer et al. |
| 5,247,343 A | 9/1993 | Burch |
| 5,303,710 A | 4/1994 | Bashkansky et al. |
| 5,362,478 A | 11/1994 | Desai et al. |
| 5,439,686 A | 8/1995 | Desai et al. |
| 5,459,570 A | 10/1995 | Swanson et al. |
| 5,498,421 A | 3/1996 | Grinstaff et al. |
| 5,505,932 A | 4/1996 | Grinstaff et al. |
| 5,508,021 A | 4/1996 | Grinstaff et al. |
| 5,512,268 A | 4/1996 | Grinstaff et al. |
| 5,560,933 A | 10/1996 | Soon-Shiong et al. |
| 5,635,207 A | 6/1997 | Grinstaff et al. |
| 5,639,473 A | 6/1997 | Grinstaff et al. |
| 5,648,506 A | 7/1997 | Desai et al. |
| 5,650,156 A | 7/1997 | Grinstaff et al. |
| 5,665,382 A | 9/1997 | Grinstaff et al. |
| 5,665,383 A | 9/1997 | Grinstaff et al. |
| 5,914,806 A | 6/1999 | Gordon, II et al. |
| 5,930,026 A | 7/1999 | Jacobson et al. |

(Continued)

FOREIGN PATENT DOCUMENTS

WO    WO 00/42906    7/2000

(Continued)

OTHER PUBLICATIONS

Lee et al., "Engineered microsphere contrast agents for optical coherence tomography", Sep. 1, 2003, Optics Letters, vol. 28, No. 17, pp. 1546-1548.*

(Continued)

*Primary Examiner*—Brian Casler
*Assistant Examiner*—Nasir Shahrestani
(74) *Attorney, Agent, or Firm*—Evan Law Group LLC

(57) ABSTRACT

A method of forming an image of a sample, comprising: forming an image of a mixture, by exposing the mixture to electromagnetic radiation; wherein the mixture comprises the sample and plasmon-resonant nanoparticles, and wherein the electromagnetic radiation is in the frequency range of infrared to ultraviolet light.

13 Claims, 4 Drawing Sheets

U.S. PATENT DOCUMENTS

| | | | |
|---|---|---|---|
| 5,972,493 | A | 10/1999 | Iwasaki et al. |
| 6,002,480 | A | 12/1999 | Izatt et al. |
| 6,068,600 | A | 5/2000 | Johnson et al. |
| 6,108,081 | A | 8/2000 | Holtom et al. |
| 6,156,292 | A | 12/2000 | Quay |
| 6,159,445 | A * | 12/2000 | Klaveness et al. ............ 424/9.6 |
| 6,208,886 | B1 | 3/2001 | Alfano et al. |
| 6,219,137 | B1 | 4/2001 | Vo-Dinh |
| 6,231,834 | B1 | 5/2001 | Unger et al. |
| 6,246,892 | B1 | 6/2001 | Chance |
| 6,246,901 | B1 | 6/2001 | Benaron |
| 6,249,271 | B1 | 6/2001 | Albert et al. |
| 6,262,706 | B1 | 7/2001 | Albert et al. |
| 6,262,833 | B1 | 7/2001 | Loxley et al. |
| 6,264,917 | B1 | 7/2001 | Klaveness et al. |
| 6,264,918 | B1 | 7/2001 | Johnson et al. |
| 6,280,704 | B1 | 8/2001 | Schutt et al. |
| 6,300,932 | B1 | 10/2001 | Albert |
| 6,307,633 | B1 | 10/2001 | Mandella et al. |
| 6,307,634 | B2 | 10/2001 | Hitzenberger et al. |
| 6,312,304 | B1 | 11/2001 | Duthaler et al. |
| 6,315,981 | B1 | 11/2001 | Unger |
| 6,344,272 | B1 | 2/2002 | Oldenburg et al. |
| 6,363,163 | B1 | 3/2002 | Xu et al. |
| 6,428,811 | B1 * | 8/2002 | West et al. .................. 424/497 |
| 6,485,413 | B1 | 11/2002 | Boppart et al. |
| 6,514,767 | B1 | 2/2003 | Natan |
| 6,529,277 | B1 | 3/2003 | Weitekamp |
| 6,530,944 | B2 | 3/2003 | West et al. |
| 6,538,805 | B1 | 3/2003 | Norwood et al. |
| 6,539,156 | B1 | 3/2003 | Dickson et al. |
| 6,564,087 | B1 | 5/2003 | Pitris et al. |
| 6,574,401 | B2 | 6/2003 | Neuberger et al. |
| 6,584,335 | B1 | 6/2003 | Haar et al. |
| 6,618,423 | B1 | 9/2003 | Dekorsy et al. |
| 6,795,777 | B1 | 9/2004 | Scully et al. |
| 6,825,928 | B2 | 11/2004 | Liu et al. |
| 6,839,586 | B2 | 1/2005 | Webb |
| 2002/0028993 | A1* | 3/2002 | Hainfeld .................... 600/420 |
| 2002/0054912 | A1 | 5/2002 | Kim et al. |
| 2002/0087071 | A1* | 7/2002 | Schmitz et al. ............. 600/420 |
| 2002/0168161 | A1 | 11/2002 | Price et al. |
| 2003/0045798 | A1 | 3/2003 | Hular et al. |
| 2003/0068496 | A1 | 4/2003 | Wei et al. |
| 2003/0082104 | A1* | 5/2003 | Mertelmeier ................ 424/9.4 |
| 2004/0023415 | A1* | 2/2004 | Sokolov et al. ............. 436/518 |
| 2004/0024307 | A1* | 2/2004 | Golman et al. ............. 600/420 |
| 2004/0058458 | A1 | 3/2004 | Anker et al. |
| 2004/0249268 | A1 | 12/2004 | Da Silva |
| 2005/0004453 | A1 | 1/2005 | Tearney et al. |
| 2005/0078363 | A1 | 4/2005 | Gugel |
| 2005/0149002 | A1* | 7/2005 | Wang et al. ..................... 606/1 |
| 2005/0168735 | A1 | 8/2005 | Boppart et al. |
| 2006/0066848 | A1 | 3/2006 | Frankel |
| 2006/0192969 | A1 | 8/2006 | Marks et al. |
| 2006/0285635 | A1 | 12/2006 | Boppart et al. |
| 2006/0292839 | A1* | 12/2006 | Yi et al. ...................... 438/570 |

FOREIGN PATENT DOCUMENTS

| | | |
|---|---|---|
| WO | WO 2007/027194 | 3/2007 |

OTHER PUBLICATIONS

Ai et al., "Electrostatic layer-by-layer nanoassembly on biological microtemplates: platelets", Biomacromolecules, 3:560-564, 2002.

Amsden et al., "An examination of factors affecting the size, distribution, and release characteristics of polymer microbeads made using electrostatics", J. Control. Release, 43:183-196, 1997.

Amsden, "The production of uniformly sized polymer microspheres", Pharm. Res., 16:1140-1143, 1999.

Boppart, "Surgical Diagnostics, Guidance, and Intervention Using Optical Coherence Tomography", Ph.D. Thesis, Massachusetts Institute of Technology, Cambridge, MA, 226 pages 1998.

Burns et al., "Tumor-localizing and photosensitizing properties of hematoporphyrin derivative in hamster buccal pouch carcinoma", Oral Surg. Oral Med. Oral Pathol., 61:368-372, 1986.

Caruso et al., "Nanoengineering of inorganic and hybrid hollow spheres by colloidal templating", Science, 282:1111-1114,1998.

Decher "Fuzzy Nanoassemblies: Toward Layered Polymeric Multicomposites", Science, 277:1232-1237, 1997.

Desai et al., "Controlled and targeted drug delivery with biocompatible protein shell microspheres", 20th Annual Meeting of Society of Biomaterials, Apr. 4-9, 1994, Boston, MA: Proc. Soc. Biomaterial, 20:112, 1994.

Dick et al., "Computed tomography of experimental liver abscesses using a new liposomal contrast agent", Investigative Radiology, 31:194-203, 1996.

Fu et al., "Visual evidence of acidic environment within degrading poly(lactic-co-glycolic acid) (PLGA) microspheres", Pharmaceutical Research, 17:100-106, 2000.

Geny et al., "Safety of a new transpulmonary echocontrast agent (Albunex®) in repeated echocardiographic studies in patients", Clin. Cardiol., 20:111-115, 1997.

Gram, "Drug absorption and distribution", in Modern Pharmacology with Clinical Applications $5^{th}$ Ed., Craig et al., eds., Little, Brown, & Co., Inc.; Boston, MA, pp. 13-24, 1997.

Grinstaff et al., "Air-filled proteinaceous microbubbles: synthesis of an echo-contrast agent", Proc. Natl. Acad. Sci. USA, 88:7708-7710, 1991.

Jue et al., "Addition of sulfhydryl groups to *Escherichia coli* ribosomes by protein modification with 2-iminothiolane (methyl 4-mercaptobutyrimidate)", Biochemistry, 17:5399-5406, 1978.

Kim et al., "Hollow silica spheres of controlled size and porosity by sol-gel processing", J. Am. Ceram. Soc., 74:1987-1992, 1991.

Kim et al., "Fabrication of hollow silica aerogel spheres by a droplet generation method and sol-gel processing" J. Vac. Sci., Technol, A., 7:1181-1184, 1989.

Kolbeck, "The biomedical applications of protein microspheres", Ph.D. Doctoral Thesis, University of Illinois, Urbana-Champaign, title page and pp. 153, 159-160, 1999.

Korbelik et al., "Photofrin accumulation in malignant and host cell populations of various tumours", British Journal of Cancer, 73:506-513, 1996.

Langer "Drug delivery and targeting", Nature, 392:5-10, 1998.

Lasic et al., "Liposomes revisited", Science, 267:1275-1276, 1995.

Leelarasamee et al., "A method for the preparation of polylactic acid microcapsules of controlled particle size and drug loading", J. Microencapsulation, 5:147-157, 1988.

Liu et al., "In vivo measurement of oxygen concentration using sonochemically synthesized microspheres", Biophysical J., 67:896-901, 1994.

Lvov et al., "Nanoparticle/polyion assembly on microtemplates (lipid tubules and latex spheres)", Colloids and Surfaces B: Biointerfaces, 23:251-256, 2002.

Lvov et al., "Thin film nanofabrication via layer-by-layer adsorption of tubule halloysite, spherical silica, proteins and polycations", Colloids and Surfaces A: Physicohem. Eng. Aspects, 198-200:375-382, 2002.

Marks et al., 'Nonlinear interferometric vibrational imaging, E-print@arxiv.org/physics/0311071, URL http://www.arxiv.org/abs/physics/0311071, pp. 1-5, 2003.

Marks et al., "Pulse shaping strategies for nonlinear interferometric vibrational imaging optimized for biomolecular imaging", Conference Proceeding: EMBC 2004: 26th Annual International Conference of the Engineering in Medicine and Biology Society (Sep. 1-5, 2004, San Francisco, CA), vol. 2, pp. 5300-5303 (accession No. 8255487).

Mathias et al., "Tumor-selective radiopharmaceutical targeting via receptor-mediated endocytosis of Gailium-67-deferoxamine-folate", J. of Nuclear Medicine, 37:1003-1008, 1996.

McNamara III et al., "Sonoluminescence temperatures during multibubble cavitation", Nature, 401:772-775,1999.

Mohwald, "From Langmuir monolayers to nanocapsules", Colloids and Surfaces A: Physicochem. Eng. Aspects, 171:25-31, 2000.

Peters, All about Albumin, in Biochemistry, Genetics, and Medical Applications, (Academic Press, New York), p. 46, 1996.

Pinkerton et al., "Aerosolized fluorescent microspheres detected in the lung using confocal scanning laser microscopy", Microscopy Research and Technique, 26:437-443, 1993.

Sansdrap et al., "Influence of manufacturing parameters on the size characteristics and the release profiles of nifedipine from poly(DL-lactide-co-glycolide) microspheres", International Journal of Pharmaceutics, 98:157-164, 1993.

Shiga et al., "Preparation of Poly(D,L-lactide) and Copoly(lactide-glycolide) Microspheres of Uniform Size", J. Pharm. Pharmacol., 48:891-895, 1996.

Suslick et al., "Protein Microencapsulation of Nonaqueous Liquids", J. Am. Chem. Soc., 112:7807-7809, 1990.

Suslick et al., "Versatile sonochemical reaction vessels" in Experimental Organometallic Chemistry: A Practicum in Synthesis and Characterization, (A. Wayda, Darensburg MY, eds. ACS Symposium Series, Washington, D.C.), pp. 195-197, 1987.

Suslick, "Sonochemistry", Science, 247: 1439-1445, 1990.

van der Laan et al., "In vitro activity of novel antifolates against human squamous carcinoma cell lines of the head and neck with inherent resistance to methotrexate", Int. J. Cancer, 51:909-914, 1992.

Violante et al., "Improved detectability of VX2 carcinoma in the rabbit liver with contrast enhancement in computed tomography", Radiology, 134:237-239, 1980.

Wang et al., "Semiconductor quantum dot-labeled microsphere bioconjugates prepared by stepwise self-assembly", Nano Lett., 2:857-861, 2002.

Webb et al., "Sonochemically produced fluorocarbon microspheres: a new class of magnetic resonance imaging agent", J. Magnetic Resonance Imaging, 6:675-683, 1996.

Wong et al., "Sonochemically produced hemoglobin microbubbles", Mat. Res. Soc. Symp. Proc., 372:89-94, 1995.

Marks et al., "Interferometric differentiation between resonant Coherent Anti-Stokes Raman Scattering and nonresonant four-wave-mixing processes", arXiv:physics/0403007, pp. 1-8, 2004.

Vinegoni et al., "Nonlinear optical contrast enhancement for optical coherence tomography", Optics Express, vol. 12, No. 2, p. 331-341, 2004.

Kee et al., "Simple approach to one-laser, broadband coherent anti-Stokes Raman scattering microscopy", Optics Letters, vol. 29, No. 23, p. 2701-2703, 2004.

Kano et al., "Vibrationally resonant imaging of a single living cell by supercontinuum-based multiplex coherent anti-Stokes Raman scattering microspectroscopy", Optics Express, vol. 13, Issue 4, pp. 1322-1327, 2005.

Gao et al., "Formulation, Characterization, and Sensing Applications of Transparent Poly(vinyl alcohol)-Polyelectrolyte Blends", Chem. Mater., 10, pp. 2481-2489, 1998.

Marks et al., Molecular Species Sensitive Optical Coherence Tomography Using Coherent Anti-Stokes Raman Scattering Spectroscopy, Coherence Domain Optical Methods and Optical Coherence Tomography In Biomedicine VII, Proceedings of SPIE, vol. 4956, pp. 9-13, 2003.

Bredfeldt et al., "Non-linear interferometric vibrational imaging", Conference on Lasers and Electro-optics, CLEO '03, pp. 309-311, 2003.

Vinegoni et al., "Nonlinear optical contrast enhancement for optical coherence tomography", http://www.arxiv.org/abs/physics/0312114, 13 pages (2003).

Zumbusch et al., "Three-dimensional vibrational imaging by coherent anti-Stokes Raman scattering", Phys. Rev. Lett., 82(20), pp. 4142-4145, 1999.

Cheng et al., "An epi-detected coherent anti-Stokes Raman scattering (E-CARS) microscope with high spectral resolution and high sensitivity", J. Phys. Chem, 105(7), pp. 1277-1280, 2001.

Hashimoto et al., "Molecular vibration imaging in the fingerprint region by use of coherent anti-Stokes Raman scattering microscopy with a collinear configuration", Opt. Lett., 25(24), pp. 1768-1770, 2000.

Volkmer et al., "Vibrational imaging with high sensitivity via epidected coherent anti-Stokes Raman scattering microscopy", Phys. Rev. Lett., 87(2):023901-1-4, 2001.

Balasubramanian R, et al. Dispersion and stability studies of resorcinarene-encapsulated gold nanoparticles. Langmuir 18:3676-81, 2002.

Balasubramanian R, Xu J, Kim B, Sadtler B, Wei A. Extraction and dispersion of large gold nanoparticles in organic solvents. J. Dispers. Sci. Tech. 22:485-89, 2001.

Blackwell HE, O'Leary DJ, Chatterjee AK, Washenfelder RA, Bussmann DA, Grubbs RH. New approaches to olefin cross-metathesis. J. Am. Chem. Soc. 122:58-71, 2000.

Boppart, S.A., "Endoscopic Optical Coherence Tomography Imaging of Barrett's Esophagus" M.D. Thesis, Harvard University, 2000.

Boppart SA, Herrmann J, Pitris C, Stamper DL, Brezinksi ME, Fujimoto JG. High-Resolution Optical Coherence Tomography-Guided Laser Ablation of Surgical Tissue. J. Surg. Res., 82:275-84, 1999.

Boyer, d., et al., Photothermal Imaging of Nanometer-Sized Metal Particles Among Scatterers, Science, 297:1160-63, 2002.

Cain, C., et al., "Visible Retinal Legions from Ultrashort Laser Pulses in the Primate Eye", Invest. Opthmalmol. Vis. Sci., 36:879-888, 1995.

Cain CP, Toth CA, Noojin GD, Carothers V, Stolarski DJ, Rockwell BA. Thresholds for Visible Lesions in the Primate Eye Produced by Ultrashort Near-Infrared Laser Pulses. Invest. Opthalmol. Vis. Sci., 40:2343-49, 1999.

Cepak VM, Martin CR. Preparation and Stability of Template-Synthesized Metallic nanorod Sols in Organic Solvents. J. Phys. Chem. B 102:9985-90, 1998.

Clark HA, Campagnola PJ, Wuskell JP, Lewis A, Loew LM. Second harmonic generation properties of fluorescent polymer-encapsulated gold nanoparticles. J. Am. Chem. Soc. 122:10234-35, 2000.

deBoer, J., et al., "Two-Dimensional Birefringence Imaging in Biological Tissue by Polarization Sensitive Optical Coherence Tomography", Opt. Lett., 22:934-36, 1997.

Dowlatshahi, K., et al., "Histological Evaluation of Rat Mammary Tumor Necrosis By Interstitial Nd:YAG Laser Hyperthermia" Lasers. Surg. Med., 12:159-164, 1992.

El-Sayed, M. A. Some interesting properties of metals confined in time and nanometer space of different shapes. Acc. Chem. Res. 34:257-64, 2001.

Freeman RG, Grabar KC, Allison KJ, Bright RM, Davis JA, Guthrie AP, Hommer MB, Jackson MA, Smith PC, Walter DG, Natan MJ.Self-Assembled Metal Colloid Monolayers: An Approach to SERS Substrates Science 267:1629-1632, 1995.

Gimenez-Conti IB, Slaga TJ. The hamster cheek pouch carcinogenesis model. J. Cell. Biochem. 17F:83-90, 1993.

Grubbs RH, Miller SJ, Fu GC. Ring-Closing Metathesis and Related Processes in Organic Synthesis. Ace. Chem. Res. 28:446-52, 1995.

Haes AJ, van Duyne RP. A nanoscale optical biosensor: sensitivity and selectivity of an approach based on the localized surface plasmon resonance spectroscopy of triangular silver nanoparticles. J. Am. Chem. Soc. 124:10596-604, 2002.

Handley DA, Arbeeny CM, White LD, Chien S. Colloidal gold-low density lipoprotein conjugates as membrane receptor probes. Proc. Natl. Acad. Sci. USA 78:368-71, 1981.

Handley DA, Chien S. Colloidal gold labeling studies related to vascular and endothelial function, hemostasis and receptor-mediated processing of plasma macromolecules. Fur. J. Cell. Biol. 43:163-74, 1987.

Hardikar VV, Matijevic E. Coating of nanosize silver particles with silica. J. Colloid. Interf. Sci. 221:133-36, 2000.

Harrington KJ, Spitzweg C, Bateman AR, Morris JC, Vile RG. Gene therapy for prostate cancer: current status and future prospects. J. Urology 166:1220-33, 2001.

Hartl, I., et al., "Ultrahigh-Resolution Optical Coherence Tomography Using Continuum Generation In An Air Silica Microstructure Optical Fiber", Opt. Lett. 26:608-610, 2001.

Hiergeist, K., et al. Application of magnetite ferrofluids for hyperthermia. J. Magn. Magn. Mater. 201:420-22, 1999.

Jackson JB. Halas NJ. Silver Nanoshells: Variations in Morphologies and optical properties. J. Phys. Chem. B 105:2743-46, 2001.

Jana NR, Gearheart L, Murphy CJ. Wet chemical synthesis of high aspect ratio cylindrical gold nanorods. Ibid. 105:4065-67, 2001.

Jang, I., "Visualization of Coronary Atherosclerotic Plaques in Patients Using Optical Coherence Tomography: Comparison With Intravascular Ultrasound", J. Am. Coll. Cardiol., 39:604-609, 2002.

Jensen T, Kelly L, Lazarides A, Schatz GC. Electrodynamics of noble metallic nanoparticles and nanoparticle clusters. J. Cluster Sci. 10:295-317, 1999.

Jin R, Cao Y, Mirkin CA, Kelly KL, Schatz GC, Zheng JG. Photoinduced conversion of silver nanospheres to nanoprisms. Science 294:1901-03, 2001.

Jordan A, Scholz R, Wust P, Fahling H, Felix R. Magnetic fluid hyperthermia (MFH): Cancer treatment with AC magnetic field induced excitation of biocompatible superparamagnetic nanoparticles. J. Magn. Magn. Mater. 201:413-19, 1999.

Kempka G, Kolb-Bachofen V. Binding, uptake, and transcytosis of ligands for mannose-specific receptors in rat liver: an electron microscopic study. Exp Cell Res 176, 38-48, 1988.

Keye, W., et al., "Argon Laser Therapy of Endometriosis: A Review of 92 Consecutive Patients" Fertil. Steril., 47:208-212, 1987.

Kim B, Tripp SL, Wei A. Self-Organization of Large Gold Nanoparticle Arrays. J. Am. Chem. Soc. 123:7955-56, 2001.

Kim F, Song JH, Yang P. Photochemical synthesis of gold nanorods. J. Am. Chem. Soc. 124:14316-17, 2002.

Kneipp, K., et al., "Ultrasensitive Chemical Analysis by Raman Spectroscopy", Chem. Rev., 99:2957-75, 1999.

Kolb-Bachofen V, Schlepper-Schafer J, Vogell W, Kolb H. Electron microscopic evidence for an asialoglycoprotein receptor on Kupffer cells: localization of lectin-mediated endocytosis. Cell 29:859-66, 1982.

Lee TM, Oldenburg AL, Sitafalwalla S, Marks, DL, Luo W, Toublan FJJ, Suslick KS, Boppart SA. Engineered microsphere contrast agents for optical coherence tomography. Opt. Lett., vol. 28, No. 17, pp. 1546-1548, 2003.

Leitgeb, It, Wojtkowski, M., Kowalczyk, A., Hitzenberger, C. K., Sticker, M., and Fercher, A. F. Spectral measurement of absorption by spectroscopic frequency-domain optical coherence tomography. Opt. Lett. 25:820-22, 2000.

Li AP, Muller F, Birner A, Nielsch K, Gösele U. Polycrystalline nanopore arrays with hexagonal ordering on aluminum. J. Vac. Sci. Technol. A, 17:1428-31, 1999.

Li F., Zhang L, Metzger RM. On the growth of highly ordered pores in anodized aluminum oxide. Chem. Mater. 10:2470-80, 1998.

Li, X., et al., Optical Coherence Tomography: Advanced Technology for the Endoscopic Imaging of Barrett's Esophagus, Endoscopy, 32:921-930, 2000.

Li, X., et al., "Imaging Needle for Optical Coherence Tomography", Opt. Lett., 25:1520-1522, 2000.

Licha, K. Contrast agents for optical imaging. Topics Curr. Chem. 222:1-29, 2002.

Lin, C., et al., "Intraocular Microsurgery with a Picosecond Nd:YAG Laser", Lasers Surg. Med. 15:44-53, 1994.

Lin SP, Wang L, Jacques SL, Tittel FK. Measurement of tissue optical properties by the use of oblique-incidence optical fiber reflectometry. Appl. Opt. 36:136-43, 1997.

Liu Q, Xu Z, Finch JA, Egerton R. A novel two-step silica-coating process for engineering magnetic nanoparticles, Chem. Mater. 10:3936-40, 1998.

Liz-Marzan LM, Giersig M, Mulvaney P. Homogeneous silica coating of vitreophobic colloids. Chem. Conunun. 731-32, 1996.

Marks, D., et al., "Study of an Ultrahigh-Numerical Aperture Fiber Continuum Generation Source For Optical Coherence Tomography", Opt. Lett., 27:2010-2012, 2002.

Masuda H., Fukada K. Ordered metallic nanohole arrays made by a two-step replication of honeycomb structures of anodic alumina. Science 268:1466-68, 1995.

Micali, N., et al., "Separation of Scattering and Absorption Contributions in UV/Visible Spectra of Resonant Systems", Anal. Chem., 73:4958-63, 2001.

Minton, J., et al., "The Laser in Surgery. A 23 Year Perspective.", Am. J. Surg., 151:725-729, 1986.

Mock JJ, Barbic M, Smith DR, Schultz DA, Schultz SJ. Shape effects in plasmon resonance of individual colloidal silver nanoparticles. J. Chem. Phys. 116:6755-59, 2002.

Mock JJ, Oldenburg SJ, Smith DR, Schultz DA, Schultz S. Composite plasmon resonant nanowires. Nano. Lett 2:465-69, 2002.

Morgner U, Drexler W, Kartner FX, Li XD, Pitris C, Ippen EP, Fujimoto JG. Spectrosopic optical coherence tomography. Opt. Lett., 25:111-13, 2000.

Nicewarner-Pena Sr., et al. Submicrometer metallic barcodes. Science 294:137-41, 2001.

Nielsch K, Choi J, Schwirn K, Wehrspohn RB, Gösele U. Self-ordering regimes of porous alumina: the 10% porosity rule. Nano Lett. 2:677-80, 2002.

Novak J, Nickerson C, Franzen S, Feldheim, DL. Purification of molecularly bridged metallic nanoparticle arrays by centrifugation and size exclusion chromatography. Anal. Chem. 73:5758-61, 2001.

Oldenburg, S., et al., "Light Scattering From Dipole and Quadrupole Nanoshell Antennas", Appl. Phys. Lett., 75:1063-65, 1999.

Pasternack, R., et al., "Resonance Light Scattering" A New Technique For Studying Chromophore Aggregation, Science, 269:935-39, 1995.

Pathak I, Davis NL, Hsiang YN, Quenville NF, Palcic B. Detection of squamous neoplasia by fluorescence imaging comparing porfimer sodium fluorescence to tissue autofluorescence in the hamster cheek pouch model. Am. J. Surg. 170:423-426, 1995.

Profio AE, Doiron DR. Transport of light in tissue in photodynamic therapy of cancer. Photochem. Photobiol. 46:591-99, 1987.

Prudhomme, M., et al., "Interstitial Diode Laser Hyperthermia in the Treatment of Subcutaneous Tumor", Laser Surg. Med. 19:445-450, 1996.

Pusztay SV, Wei A, Stavens KB, Andres RP. Encagement of Gold Nanoclusters in Crosslinked Resorcinarene Shells. Supramol. Chem. 14:291-94, 2002.

Quaroni L, Chumanov G. Preparation of Polymer-Coated Functionalized Silver Nanoparticles. J. Am. Chem. Soc. 121:10642-43, 1999.

Sadtler B, Wei A. Spherical ensembles of gold nanoparticles on silica: electrostatic and size effects. Chem. Commun., 1604-05, 2002.

Schaefer, A., et al., "Real-Time Digital Signal Processing-Based Optical Coherence Tomography and Doppler Optical Coherence Tomography", IEEE Transactions on Biomedical Engineering, vol. 51, No. 1, pp. 186-190, 2004.

Schmitt JM, Knuttel A, Bonner RF. Measurements of optical properties of biological tissues by low-coherence reflectometry. Appl. Opt. 32:6032-42, 1993.

Schmitt JM, Knuttel A, Yadlowsky M, Eckhaus AA. Optical coherence tomography of a dense tissue: statistics of attenuation and backscattering. Phys. Med. Biol. 39:1705-20, 1994.

Sevick-Muraca EM, Houston JP, Gurfinkel, M. Fluorescence-enhanced, near infrared diagnostic imaging with contrast agents. Curr. Op. Chem. Biol. 6:642-50, 2002.

Shipway AN, Katz E, Willner I. Nanoparticle arrays on surfaces for electronic, optical, and sensor applications. ChemPhysChem 1:18-52, 2000.

Slaga TJ, Gimenez-Conti IB. An animal model for oral cancer. J. Natl. Cancer Inst. Monogr. 13:55-60, 1992.

Sönnichsen C, Franzl T, Wilk T, von Plessen G, Feldmann J. Drastic reduction of plasmon damping in gold nanorods. Phys. Rev. Lett. vol. 88, No. 7:077402-1-077402-4, 2002.

Sönnichsen, C., et al., "Spectroscopy of Single Metallic Nanoparticles Using Total Internal Reflection Microscopy", Appl. Phys. Lett., 75:77:2949-51, 1999.

Stavens KB, Pusztay SV, Zou S, Andres RP, Wei A. Encapsulation of Neutral Gold Nanoclusters by Resorcinarenes. Langmuir 15:8337-39, 1999.

Tanaka K, Mitsushima A, Yamagata N, Kashima Y, Takayama H. Direct visualization of colloidal gold-bound molecules and a cell-surface receptor by ultrahigh-resolution scanning electron microscopy. J. Microsc. 161:455-61. 1991.

Tearney GI, Brezinski ME, Bouma BE, Boppart SA, Pitris C, Southern JF, Fujimoto JG. In vivo endoscopic optical biopsy with optical coherence tomography. Science. 276:2037-39, 1997.

Tearney, G.J., et al., "High-Speed Phase- and Group-Delay Scanning with a Grating-Based Phase Control Delay Line", Opt. Lett., vol. 27, No. 23 :1811-1813, 1997.

Templeton AC, Wuelfing MP, Murray RW. Monolayer protected cluster molecules. Acc. Chem. Res. 33:27-36, 2000.

Timmerman P, Verboom W, Reinhoudt DN., "Resorcinarenes" Tetrahedron 52:2663-704, 1996.

Toth CA, Cain CP, Stein CD. et al. Retinal effects of ultrashort laser pulses in the rabbit eye. Invest. Opthalmol. Vis. Sci. 36:1910-17, 1995.

Tripp SL, Pusztay SV, Ribbe AE, Wei A. Self-assembly of cobalt nanoparticle rings. J. Am. Chem. Soc. 124:7914-15, 2002.

Ung T, Liz-Marzan LM, Mulvaney P. Controlled method for silica coating of silver colloids. Influence of coating on the rate of chemical reactions. Langmuir 14:3740-48, 1998.

Van der Smissen P, Courtoy PJ, Baudhuin P. Quantitative analysis of clustering on biological membranes: methodology and application to ligandinduced asialoglycoprotein receptor redistribution on rat hepatocytes. Eur. J. Cell. Biol. 69:45-54, 1996.

Van der Smissen P, Vael T, Courtoy PJ, Baudhuin P. Ligand-induced clustering of asialoglycoprotein receptors on rat hepatocytes at 4° C. Eur. J. Cell. Biol. 60:122-30, 1993.

van der Zande B, Böhmer MR, Fokkink, LGJ., Schonenberger, C. Colloidal dispersions of gold rods: synthesis and optical properties. Langmuir 16:451-58, 2000.

Vitkin A, Woolsey J, Wilson BC, Anderson RR. Optical and thermal characterization of natural (sepia officinalis) melanin. Photochem. Photobiol. 59:455-62, 1994.

Vo-Dinh, T., "Surface-Enhanced Raman Spectroscopy Using Metallic Nanostructures", Trends Anal. Chem. Soc., 17:557-82, 1998.

Wang, L., et al., Use of Laser Beam with an Oblique Angle of Incidence to Measure the Reduced Scattering Coefficient of a Turbid Medium, Appl. Opt., 34:2362-2366, 1995.

Wei A, Kim B, Pusztay SV, Tripp SL, Balasubramanian R. Resorcinarene-encapsulated nanoparticles: building blocks for self-assembled nanoparticles. J. Inclusion Phenom. Macrocyclic Chem., 2001, 41, 83-86.

Wei, A., et al., "Tunable Surface-Enhanced Raman Scattering from Large Gold Nanoparticle Arrays", ChemPhysChem. 2:743-45, 2001.

Wei A, Stavens KB, Pusztay SV, Andres RP. Synthesis and Characterization of Resorcinarene-Encapsulated Nanoparticles. MRS Symp. Proc. Ser. 581:59-63, 1999.

Xu, H., et al., "Electromagnetic Contributions to Single-Molecule Sensitivity in Surface-Enhanced Raman Scattering", Phys. Rev. E. 62:4318-24, 2000.

Yguerabide J, Yguerabide BE. Light-scattering submicroscopic particles as highly fluorescent analogs and their use as tracer labels in clinical and biological applications. I. Theory. Anal Biochem. 262:137-56, 1998.

Yu YY, Chang SS, Lee CL., Wang CRC. Gold nanorods: electrochemical synthesis and optical properties. J Phys Chem B 101:6661-64, 1997.

Zaheer A.; Lenkinski, R. E.; Mahmood, A.; Jones, A. G.; Cantley, L. C.; Frangioni, J. V. In vivo near-infrared fluorescence imaging of osteoblastic activity. Nature Biotechnol. 19:1148-54, 2001.

Schaefer, A.W., "Real-Time Digital Signal Processing-Based Optical Coherence Tomography and Optical Doppler Tomography", Thesis, university of Illinois at Urbana-Champaign, 2001.

Gazelle, G.S., et al., "Nanoparticulate computed tomography contrast agents for blood pool and liver-spleen imaging", Acad. Radiol. 1:373-376, 1994.

Handley, D.A., "Methods for Synthesis of Colloidal Gold", Colloidal Gold: Principles, Methods, and Applications, (Academic Press), vol. 1, pp. 13-32, 1989.

Lee, T., et al., "Optical Characterization of Contrast Agents for Optical Coherence Tomography", Proceedings of SPIE, vol. 4967, pp. 129-134, 2003.

Reussell-Jones, G. J., "Use of vitamin B-12 conjugates to deliver protein drugs by the oral route", Critical Reviews in Therapeutic Drug Carrier Systems, vol. 15, No. 6, pp. 557-586, 1998.

Pollack, A., et al., "Circumferential Argon Laser Photocoagulation for Prevention of Retinal Detachment", Eye, vol. 8, pp. 419-422, 1994.

Tuting, T., "The immunology of cutaneous DNA immunization", Current Opinion in Molecular Therapeutics, vol. 1, No. 2, pp. 216-225, 1999.

Kano et al., "Vibrationally resonant imaging of a single living cell by supercontinuum-based multiplex coherent anti-Stokes Raman scattering microspectroscopy", Optics Express, vol. 13, Issue 4, pp. 1322-1327, 2005.

Gao et al., "Formulation, Characterization, and Sensing Applications of Transparent Poly(vinyl alcohol)-Polyelectrolyte Blends", Chem. Mater., 10, pp. 2481-2489, 1998.

Marks et al., Molecular Species Sensitive Optical Coherence Tomography Using Coherent Anti-Stokes Raman Scattering Spectroscopy, Coherence Domain Optical Methods and Optical Coherence Tomography In Biomedicine VII, Proceedings of SPIE, vol. 4956, pp. 9-13, 2003.

Bredfeldt et al., "Non-linear interferometric vibrational imaging", Conference on Lasers and Electro-optics, CLEO '03, pp. 309-311, 2003.

Vinegoni et al., "Nonlinear optical contrast enhancement for optical coherence tomography", http://www.arxiv.org/abs/physics/0312114, 13 pages (2003).

Zumbusch et al., "Three-dimensional vibrational imaging by coherent anti-Stokes Raman scattering", Phys. Rev. Lett., 82(20), pp. 4142-4145, 1999.

Cheng et al., "An epi-detected coherent anti-Stokes Raman scattering (E-CARS) microscope with high spectral resolution and high sensitivity", J. Phys. Chem, 105(7), pp. 1277-1280, 2001.

Volkmer et al., "Vibrational imaging with high sensitivity via epidected coherent anti-Stokes Raman scattering microscopy", Phys. Rev. Lett., 87(2):023901-1-4, 2001.

Schmitt et al., "Optical-coherence tomography of a dense tissue: statistics of attenuation and backscattering", Phys. Med. Biol., vol. 39, pp. 1705-1720, (1994).

Tearney et al., "In vivo endoscopic optical biopsy with optical coherence tomography", Science, vol. 276, pp. 2037-2039, (1997).

Fantini et al., "Assessment of the size, position, and optical properties of breast tumors in vivo by noninvasive optical methods", Applied Optics, vol. 37, pp. 1982-1989, 1998.

Faber et al., "Quantitative measurement of attenuation coefficients of weakly scattering media using optical coherence tomography", Optics Express, 12(19), pp. 4353-4365, 2004.

Fujimoto et al., "Optical Coherence Tomography: An Emerging Technology for Biomedical Imaging and Optical Biopsy", Neoplasia, 2(1-2), pp. 9-25, 2000.

Zysk et al., "Computational methods for analysis of human breast tumor tissue in optical coherence tomography images", Journal of Biomedical Optics, 11(5), 054015-1-054015-7, 2006.

Levitz et al., "Determination of optical scattering properties of highly-scattering media in optical coherence tomography images", Optics Express, 12(2), pp. 249-259, 2004.

Morgner et al., "Spectroscopic optical coherence tomography", Optics Letters, 25(2), pp. 111-113, 2000.

Gossage et al., "Texture analysis of optical coherence tomography images: feasibility for tissue classification", Journal of Biomedical Optics, 8(3), pp. 570-575, 2003.

Zvyagin et al., "Refractive index tomography of turbid media by bifocal optical coherence refractometry", Optics Express, 11(25), pp. 3503-3517, 2003.

Gottschalk, "Ein Meβverfahren zur Bestimmung der optischen Parameter biologisher Gewebe in vitro", Dissertation 93 HA 8984, Universität Fridericiana Karlsruhe, 1993.

Bolin, F.P. et al., "Refractive index of some mammalian tissues using a fiber optic cladding method", Applied Optics, 28, pp. 2297-2303, 1989.

Tearney et al., "Determination of the refractive index of highly scattering human tissue by optical coherence tomography", Optics Letters, 20(21), pp. 2258-2260, 1995.

Zysk et al., "Needle-based refractive index measurement using low-coherence interferometry", Optics Letters, 32, pp. 385-387, 2007.

Zysk et al., "Refractive index of carcinogen-induced rat mammary tumours", Phys. Med. Biol., 51, pp. 2165-2177, 2006.

Li et al., "Measurement method of the refractive index of biotissue by total internal reflection", Applied Optics, 35, pp. 1793-1795, 1996.

Knuttel et al., "Spatially confined and temporally resolved refractive index and scattering evaluation in human skin performed with optical coherence tomography", Journal of Biomedical Optics, 5, pp. 83-92, 2000.

Boppart et al., "Optical coherence tomography: feasibility for basic research and image-guided surgery of breast cancer", Breast Cancer Research and Treatment, vol. 84, pp. 85-97, 2004.

Liberman et al., "Palpable breast masses: Is there a role for percutaneous image-guided core biopsy?", American Journal of Roentgenology, vol. 175, pp. 779-787, 2000.

Bolivar et al., "Stereotaxic core needle aspiration biopsy with multiple passes in nonpalpable breast lesions", Acta Radiologica, vol. 39, pp. 389-394, 1998.

Acheson et al., "Histologic correlation of image-guided core biopsy with excisional biopsy of nonpalpable breast lesions", Archives of Surgery, vol. 132, pp. 815-821, 1997.

Pijnappel et al., "The diagnostic accuracy of core biopsy in palpable and non-palpable breast lesions", European Journal of Radiology, vol. 24, pp. 120-123, 1997.

Durduran et al., "Bulk optical properties of healthy female breast tissue", Physics in Medicine and Biology, vol. 47, pp. 2847-2861, 2002.

International Search Report dated Feb. 15, 2007 for International Application No. PCT/US2006/006618, 5 pages.

Marks et al., "Interferometric differentiation between resonant coherent anti-Stokes Raman scattering and nonresonant four-wave-mixing processes", Applied Physics Letters, vol. 85, No. 23, pp. 5787-5789, 2004.

Marks et al., "Nonlinear Interferometric Vibrational Imaging", Physical Review Letters, vol. 92, No. 12, pp. 123905-1-123905-4, 2004.

Boppart et al., "Contrast Enhancement Methods for Optical Coherence Tomography", Biophotonics/Optical Interconnects and VLSI Photonics/WBM Microactivities, 2004 Digest of the Leos Summer Topical Meetings, San Diego, CA, pp. 14-15, 2004.

Marks et al., "Pulse Shaping Strategies for Nonlinear Interferometric Vibrational Imaging Optimized for Biomolecular Imaging", Proceedings of the 26th Annual International Conference of the IEEE EMBS, San Francisco, CA, pp. 5300-5303, 2004.

Bredfeldt et al., "Nonlinear interferometric vibrational imaging of molecular species", Proc. Of SPIE, vol. 5321, pp. 149-156, 2004.

Easy Core Biopsy System, Product Brochure, Boston Scientific, 5 pages, 2004.

Yodh et al., "Spectroscopy and Imaging with Diffusing Light," Physics Today, pp. 34-40, 1995.

Roggan et al., in "Laser Induced Interstitial Thermotherapy", Muller, Ed., pp. 39-40,43, 1995.

Ohmi et al., "In Vitro Simultaneous Measurement of Refractive Index and Thickness of Biological Tissue by the Low Coherence Interferometry", IEEE Transactions on Biomedical Engineering, vol. 47, No. 9, pp. 1266-1270, 2000.

Luo et al., "Optical Biopsy of Lymph Node Morphology using Optical Coherence Tomography", Technology in Cancer Research & Treatment, vol. 4, No. 5, pp. 539-547, 2005.

Dehghani et al., "The effects of internal refractive index variation in near-infrared optical tomography: a finite element modelling approach", Physics in Medicine and Biology, 48, pp. 2713-2727, 2003.

Schmitt et al., "Turbulent nature of refractive-index variations in biological tissue", Optics Letters, vol. 21, No. 16, pp. 1310-1312, 1996.

Zysk et al., "Projected index computed tomography", Optics Letters, vol. 28, No. 9, pp. 701-703, 2003.

Easy Core Biopsy System, Product Brochure, Boston Scientific, 4 pages, 2004.

Evans et al., "Coherent anti-Stokes Raman scattering spectral interferometry: determination of the real and imaginary components of nonlinear susceptibility chi(3) for vibrational microscopy", Optics Letters, vol. 29, No. 24, pp. 2923-2925, 2004.

Yoon et al., "Dependence of line shapes in femtosecond broadband stimulated Raman spectroscopy on pump-probe timed delay", J Chem Phys., 122(2), p. 024505, 2005, 20 pages.

Kolomoitsev et al., "New problems of femtosecond time-domain CARS of large molecules", SPIE vol. 1402, pp. 31-43, 1990.

Mehendale et al, "Towards an anthrax detector using the femtosecond adaptive spectroscopic technique for coherent anti-Stokes Raman Spectroscopy: coherent anti-Stokes Raman spectroscopy signal from dipicolinic acid in bacterial spores", Journal of Modern Optics, vol. 51, pp. 2645-2653, 2004.

Barton JK, Hoying JB, Sullivan CJ. Use of microbubbles as an optical coherence tomography contrast agent, Contrast Material Research Conference, Woodstock, VT (published in supplement to "Academic Radiology," Sep. 12-17, 1999).

Boppart SA, Bouma BE, Pitris C, Southern JF, Brezinski ME, Fujimoto JG. In vivo cellular optical coherence tomography imaging. Nature Med. 4:861-64, 1998.

Boppart SA, Bouma BE, Pitris C, Tearney GJ, Fujimoto JG. Forward-imaging instruments for optical coherence tomography. Opt. Lett. 22:1618-20, 1997.

Boppart SA, Bouma BE, Pitris C, Tearney GJ, Southern JF, Brezinski ME, Fujimoto JG. Intraoperative assessment of microsurgery with three-dimensional optical coherence tomography. Radiology. 208:81-86, 1998.

Boppart SA, Brezinski ME, Bouma BE, Tearney GJ, Fujimoto JG. Investigation of developing embryonic morphology using optical coherence tomography. Dev. Biol. 177:54-63, 1996.

Boppart SA, Brezinski ME, Pitris C, Fujimoto JG. Optical Coherence Tomography for Neurosurgical Imaging of Human Intracortical Melanoma. Neurosurgery 43:834-41, 1998.

Boppart SA, Brezinski ME, Tearney GJ, Bouma BE, Fujimoto JG. Imaging developing neural morphology using optical coherence tomography. J. Neurosci. Meth. 2112:65-72, 1996.

Boppart SA, Tearney GJ, Bouma BE, Southern JF, Brezinski ME, Fujimoto JG. Noninvasive assessment of the developing *Xenopus* cardiovascular system using optical coherence tomography. Proc. Natl. Acad. Sci. USA 94:4256-61, 1997.

Bouma BE, Tearney GJ, Boppart SA, Hee MR, Brezinski ME, Fujimoto JG. High resolution optical coherence tomographic imaging using a modelocked Ti:$Al_2O_3$ laser. Opt. Lett. 20:1486-88, 1995.

Bouma BE, Tearney GJ, Compton CC, Nishioka NS. High-resolution imaging of the human esophagus and stomach in vivo using optical coherence tomography. Gastrointest. Endosc. 51:467-74, 2000.

Brezinski ME, Tearney GJ, Bouma BE, Izatt JA, Hee MR, Swanson EA, Southern JF, Fujimoto JG. Optical coherence tomography for optical biopsy: properties and demonstration of vascular pathology. Circulation 93:1206-13, 1996.

Bugaj JE, Achilefu S, Dorshow RB, Rajagopalan R. Novel fluorescent contrast agents for optical imaging of in vivo tumors based on a receptor-targeted dye-peptide conjugate platform, J. Biomed. Opt. 6:122-33, 2001.

Chen Z, Milner TE, Srinivas S, Wang X. Noninvasive imaging of in vivo blood flow velocity using optical Doppler tomography. Opt. Lett. 22:1119-21, 1997.

Christiansen C, Kryvi H, Sontum PC, Skotland T. Physical and biochemical characterization of Albunex, a new ultrasound contrast agent consisting of air-filled albumin microparticles suspended in a solution of human albumin. Biotechnol. Appl. Biochem. 19:307-20, 1994.

Drexler W, Morgner U, Kartner FX, Pitris C, Boppart SA, Li X, Ippen EP, Fujimoto JG. In vivo ultrahigh resolution optical coherence tomography. Opt. Lett. 24:1221-23, 1999.

Fujimoto JG, Brezinski ME, Tearney GJ, Boppart SA, Bouma BE, Hee MR, Southern IF, Swanson EA. Biomedical imaging and optical biopsy using optical coherence tomography. Nature Medicine 1:970-72, 1995.

Hee MR, Izatt JA, Swanson EA, Huang D, Schuman JS, Lin CP, Puliafito CA, Fujimoto JG. Optical coherence tomography of the human retina. Arch. Ophthalmol. 113:325-32, 1995.

Hirsch, L., et al., "A Whole Blood Immunoassay Using Gold Nanoshells", Analytical Chemistry, 75:2377-2381, 2003.

Huang D, Swanson EA, Lin CP, Schuman JS, Stinson WG, Chang W, Hee MR, Flotte T, Gregory K, Puliafito CA, Fujimoto JG. Optical Coherence Tomography. Science 254:1178-81, 1991.

Larson, D., et al., "Water-Soluble Quantum Dots for Multiphoton Fluorescence Imaging in Vivo", Science, 300:1434-1436, 2003.

Lee RJ, Low PS. Delivery of Liposomes to Cultured KB Cells via Folate Receptor-Mediated Endocytosis. J. Biol. Chem. 269:3198-204, 1994.

Pitris C, Goodman AK, Boppart SA, Libus JJ, Fujimoto JG, Brezinski ME. High resolution imaging of gynecological neoplasms using optical coherence tomography. Obstet. Gynecol. 93:135-39, 1999.

Pitris C, Jesser C, Boppart SA, Stamper D, Brezinski ME, Fujimoto JG. Feasibility of optical coherence tomography for high resolution imaging of human gastrointestinal tract malignancies. J. Gastroenterol. 35:87-92, 1999.

Puliafito CA, Hee MR, Lin CP, Reichel E, Schuman JS, Duker JS, Izatt JA, Swanson EA, Fujimoto JG. Imaging of macular disease with optical coherence tomography (OCT). Ophthalmology 102:217-29, 1995.

Puliafito CA, Hee MR, Schuman JS, Fujimoto JG. *Optical Coherence Tomography of Ocular Diseases*. Slack, Inc, Thorofare, NJ, 1995.

Schmitt JM, Knuttel A, Yadlowsky M, Eckhaus AA. Optical coherence tomography of a dense tissue: statistics of attenuation and backscattering. Phys. Med. Biol. 39:1705-20, 1994.

Schmitt JM, Yadlowsky MJ, Bonner RF. Subsurface imaging of living skin with optical coherence microscopy. Dermatology 191:93-98, 1995.

Sergeev AM, Gelikonov VM, Gelikonov GV, Feldchtein FI, Kuranov RV, Gladkova ND, Shakhova NM, Snopova LB, Shakov AV, Kuznetzova IA, Denisenko AN, Pochinko VV, Chumakov YP, Streltzova OS. In vivo endoscopic OCT imaging of precancer and cancer states of human mucosa. Opt Express 1:432-40, 1997.

Sivak MV Jr, Kobayashi K, Izatt JA, Rollins AM, Ung-Runyawee R, Chak A, Wong RC, Isenberg GA, Willis J. High-resolution endoscopic imaging of the gastrointestinal tract using optical coherence tomography. Gastrointest. Endosc. 51:474-79, 2000.

Sokolov, K., et al., "Real-Time Vital Optical Imaging of Precancer Using Anti-Epidermal Growth Factor Receptor Antibodies Conjugated to Gold Nanoparticles", Cancer Res.,63:1999-2004, 2003.

Su MY, Muhler A, Lao X, Nalcioglu O. Tumor characterization with dynamic contrast-enhanced MRI using MR contrast agents of various molecular weights, Magn. Reson. Med. 39:259-69, 1998.

Tearney GJ, Boppart SA, Bouma BE, Brezinski ME, Weissman NJ, Southern JF, Fujimoto 5G. Scanning single-mode fiber optic catheter-endoscope for optical coherence tomography. Opt. Lett. 21:1-3, 1996.

Tearney GJ, Bouma BE, Boppart SA, Golubovic B, Swanson EA, Fujimoto JG. Rapid acquisition of in vivo biological images using optical coherence tomography. Opt. Lett. 21:1408-10, 1996.

Tearney GJ, Brezinski ME, Boppart SA, Bouma BE, Weissman N, Southern JF, Swanson EA, Fujimoto JG. Catheter-based optical imaging of a human coronary artery. Circulation 94:3013, 1996.

Tearney, GJ, et al., "In Vivo Endoscopic Optical Biopsy with Optical Coherence Tomography", Science, 276:2037-2039, 1997.

Tearney GJ, Brezinski ME, Southern JF, Bouma BE, Boppart SA, Fujimoto JG. Optical biopsy in human gastrointestinal tissue using optical coherence tomography. Amer. J. Gastroenterol. 92:1800-04, 1997.

Tearney GJ, Brezinski ME, Southern JF, Bouma BE, Boppart SA, Fujimoto JG. Optical biopsy in human urologic tissue using optical coherence tomography. J. Ural. 157:1915-19, 1997.

Tkachenko, A., et al., "Multifunctional Gold Nanoparticle-Peptide Complexes for Nuclear Targeting", J. Am. Chem. Soc., 125:4700-4701, 2003.

F. Toublan, et al., "Magnetically-inducible optical contrast agents for optical coherence tomography", presented at the Optical Society of America Biomedical Topical Meeting, Miami, FL, Apr. 7-10, 2002.

Turkevich J, Stevenson PC, Hillier J. "A Study of the Nucleation and Growth Processes in the Synthesis of Colloidal Gold", Faraday Soc. 11:55-75, 1951.

Yazdanfar S, Kulkami MD, Izatt JA. High resolution imaging of in vivo cardiac dynamics using color Doppler optical coherence tomography. Opt. Express. 1:424-31, 1997.

\* cited by examiner

MULTI-FUNCTIONAL PLASMON-RESONANT CONTRAST AGENTS FOR OPTICAL COHERENCE TOMOGRAPHY

STATEMENT OF ACKNOWLEDGMENT OF GOVERNMENT SUPPORT

This invention was made with Government support under Contract Number NAS2-02057 awarded by the National Aeronautic and Space Administration Ames Research Center and the National Cancer Institute. The Government has certain rights in the invention.

BACKGROUND

When imaging biological tissues, it is often desirable to enhance the signals measured from specific structures. Contrast agents, which produce a strong emission or reflection signal, have been utilized in virtually every imaging modality including ultrasound [1], computed tomography [2], magnetic resonance imaging [3], and optical microscopy [4].

Optical coherence tomography (OCT) is an emerging high-resolution medical and biological imaging technology [5-11]. OCT is analogous to ultrasound B-mode imaging except reflections of low-coherence light are detected rather than sound. OCT detects changes in the backscattered amplitude and phase of light from structures in tissue. This imaging technique is attractive for medical imaging because it permits the imaging of tissue microstructure in situ, yielding micron-scale imaging resolution without the need for excision and histological processing. OCT can record structures such as cell membranes, nuclei, and other organelles based on morphology-dependent optical characteristics. Because OCT performs imaging using light, it has a one- to two-order-of-magnitude higher spatial resolution than ultrasound and does not require contact with tissue.

High-quality OCT imaging also depends on the mechanism for optical contrast. Backscatter detection is the most commonly used method of contrast generation; however, this is not necessarily the only way to obtain high contrast. Spectroscopic OCT techniques have been recently developed and can be used as an additional means for generating contrast in OCT images [12, 13]. Whereas standard OCT uses the amplitude (envelope) of the backscattered signal to generate a structural OCT image of tissue, spectroscopic OCT techniques extract data from the interference fringes (carrier) of the backscatter. By taking the Fourier or Morlet-wavelet transform over windowed regions of the interference fringes, variations in the spectrum of the reflected light can be obtained. If endogenous molecules or exogenous contrast agents have strong spectral absorption features within the bandwidth of the OCT source, the three-dimensional spatial distribution of these absorption characteristics can be imaged. Substances which exhibit strong and selective absorption signatures, such as melanin and hemoglobin, can be used to identify cell types. For example, spectroscopic OCT has been used to identify melanocytes in mesenchymal cells from the African frog tadpole [6].

In addition to spectroscopic OCT methods, Doppler OCT can be enhanced by dynamic contrast modulation, based upon changes in the phase (frequency) of the interference fringes. Doppler OCT has been used primarily to detect and quantify blood flow within biological tissue [14, 15]. Moving objects within the tissue will also induce Doppler frequency shifts in the background light.

OCT was originally developed and demonstrated in ophthalmology for high-resolution tomographic imaging of the retina and anterior eye [16-18]. Because the eye is transparent and is easily optically accessible, it is well-suited for diagnostic OCT imaging. OCT is promising for the diagnosis of retinal disease because it can provide images of retinal pathology with 10 µm resolution, almost one order-of-magnitude higher than previously possible using ultrasound. Clinical studies have been performed to assess the application of OCT for a number of macular diseases [17, 18]. OCT is especially promising for the diagnosis and monitoring of glaucoma and macular edema associated with diabetic retinopathy because it permits the quantitative measurement of changes in the retinal or retinal nerve fiber layer thickness. Because morphological changes often occur before the onset of physical symptoms, OCT can provide a powerful approach for the early detection of these diseases.

Recently, OCT has been applied for imaging a wide range of nontransparent tissues [6, 7, 919-20]. In tissues other than the eye, the imaging depth is limited by optical attenuation due to scattering and absorption. A "biological window" exists in tissue where absorption of near-infrared (NIR) wavelengths is at a minimum and light can penetrate deep into highly-scattering tissue [21]. Because optical scattering decreases with increasing wavelength, OCT in nontransparent tissues has routinely used 1.3 µm wavelength light for imaging. In most tissues, imaging depths of 2-3 mm can be achieved using a system detection sensitivity of 110 dB (1 part in $10^{11}$). OCT has been applied to image arterial pathology in vitro and has been shown to differentiate plaque morphology with superior resolution to ultrasound [7, 22].

Imaging studies have also been performed to investigate applications in gastroenterology, urology, and neurosurgery [23-25]. High resolution OCT using short coherence length, short-pulse light sources, has also been demonstrated and axial resolutions of less than 5 µm have been achieved [26, 27]. High-speed OCT at image acquisition rates of 4 to 8 frames per second for 500 to 250 square pixel images has been achieved [28]. OCT has been extended to perform Doppler imaging of blood flow and birefringence imaging to investigate laser intervention [14, 15]. Different imaging delivery systems including transverse imaging catheters and endoscopes, and forward imaging devices have been developed to enable internal body OCT imaging [29, 30]. Most recently, OCT has been combined with catheter-endoscope-based delivery to perform in vivo imaging in animal models and human patients [10, 31-33].

Apart from medical applications, OCT has been demonstrated as an emerging investigational tool for cell and developmental biology. OCT has imaged the development of numerous animal models including *Rana pipiens* and *Xenopus laevis* (Leopard and African frog), and *Brachydanio rerio* (zebrafish) [34, 35]. High-speed OCT imaging has permitted the morphological and functional imaging of the developing *Xenopus* cardiovascular system, including changes in heart function following pharmacological interventions [36]. High-resolution imaging has permitted the real-time tracking of cell dynamics in living specimens including mesenchymal cell mitosis and neural crest cell migration [37]. OCT is advantageous in microscopy applications because repeated non-invasive imaging of the morphological and functional changes in genetically modified animals can be performed overtime without having to histologically process multiple specimens. The high-resolution, cellular-imaging capabilities suggest that OCT can be used to diagnose and monitor early neoplastic changes in humans.

The ability of OCT to perform optical biopsies, the in situ imaging of tissue microstructure at near-histological resolution, has been used to image morphological differences between normal and neoplastic tissue. OCT images of in vitro neoplasms of the female reproductive tract [38], the gastrointestinal tract [39], and the brain [25] have been investigated. Optical differences between normal and neoplastic tissue were evident, but primarily for late-stage changes. Still, situations exist where no inherent optical contrast exists between normal and pathologic tissue, such as in early-stage, pre-malignant tumors or in tumors which remain optically similar to normal tissue.

In the past, OCT has found numerous medical and biological applications. However, the imaging technique has relied largely on the inherent optical properties of the tissue to provide contrast and differentiate normal from pathological tissue. Phospholipid-coated perfluorobutane microbubbles (ImaRx Pharmaceutical, Tucson, Ariz.) have been used as a contrast agent for OCT. Although such microbubbles produce a strong OCT signal, blood and tissue also produce fairly strong OCT signals, and the effects of this contrast agent in vivo on the visualization of blood vessels are subtle [40].

Despite the rapidly growing acceptance of OCT in biomedical imaging, there are presently few agents available for enhancing optical contrast. This is partly attributable to the use of NIR wavelengths (>800 nm) that are typically employed in OCT, which are outside the range of most optically active materials. The keen demand for new optical imaging methods has spurred the development of NIR-active contrast agents [41]. Some of the materials currently under investigation include carbon black, melanin, and colloidal particles [42-44]. NIR fluorescent dyes have been reported to produce detectable emissions at micromolar concentrations, and are potential contrast agents because specific spectral features can be detected using spectroscopic OCT techniques [45, 46].

Site-directed hyperthermia has long been considered as an attractive and possibly noninvasive alternative to surgery, in which a localized heat source is directed toward the eradication of diseased tissue. Generation of hyperthermia in biological cells and tissues has been shown to compromise the resistance of tissues to chemotherapy or radiation, or result in necrosis at higher temperatures [47]. Noninvasive hyperthermia can be achieved using nanometer-sized particles; for example, the exposure of a suspension of magnetically active colloids to an AC magnetic field produces a temperature increase due to localized magnetothermal effects, with various power loss mechanisms contributing to heat transfer [48].

SUMMARY

In a first aspect, the present invention is a method of forming an image of a sample that includes forming an image of a mixture by exposing the mixture to electromagnetic radiation in the frequency range of infra-red to ultraviolet light. The mixture contains the sample and plasmon-resonant nanoparticles.

In a second aspect, the present invention is a method of destroying tissue, that includes administering anisotropic metallic nanoparticles to the tissue to form a mixture and subjecting the mixture to electromagnetic radiation.

In a third aspect, the present invention is an improved method of forming an image by optical coherence tomography, that includes exposing a patient to electromagnetic radiation, collecting reflected electromagnetic radiation, and forming an image from the collected electromagnetic radiation. The improvement is drawn to administering anisotropic metallic nanoparticles to the patient to enhance contrast of the image. Further, the anisotropic metallic nanoparticles include gold nanorods with a magnetic tip.

In a fourth aspect, the present invention is a method of forming an image of a sample that includes forming an image of a mixture by exposing the mixture to electromagnetic radiation. The mixture includes the sample and metallic nanoparticles composed of gold, silver, or copper.

Definitions

The phrase "a compositional modification" means a modification that results in a change in the chemical composition of a nanoparticle, such as the addition of gold to a nanoparticle comprising silver.

The phrase "a surface modification" means a modification that results in the addition of a small molecule or ligand to the surface of a nanoparticle, such as the conjugation of folate to the surface of a gold nanoparticle.

The phrase "enhancing the contrast" means that an image produced with the enhancement shows a greater difference in adsorbed, scattered or reflected electromagnetic radiation between parts of the image, than an otherwise identical image produced without the enhancement.

The term "image" means data produced by receipt of electromagnetic radiation, which may or may not be formed into a picture viewable by the human eye. This includes images produced directly onto a medium such as film or video.

The phrase "infrared to ultraviolet" means electromagnetic radiation having a frequency of $10^{12}$ to $10^{17}$ Hz, which excludes radio waves, microwaves, X-rays and gamma rays.

The term "light" means visible light.

The term "nanoparticle" refers to a particle that has a longest axis with a length of at most one micrometer.

The term "nanoellipsoid" refers to a nanoparticle that is shaped like an ellipsoid.

The term "nanorod" refers to a nanoparticle that is shaped like a rod.

The term "nanosphere" refers to a nanoparticle that is spherical.

The term "nanotriangle" refers to a nanoparticle that is shaped like a triangle.

The term "surface plasmons" refers to collective electronic excitations that enhance the optical response of metal particles at a frequency (e.g., displaying an extinction coefficient of at least $10^6$ M$^{-1}$cm$^{-1}$).

The phrase "plasmon-resonant nanoparticles" refers to metallic nanopaticles that have an extinction coefficient of at least $10^6$ M$^{-1}$cm$^{-1}$ at some frequency in the range of $10^{12}$ to $10^{17}$ Hz.

The phrase "plasmon-resonant contrast agent" refers to plasmon-resonant nanoparticles suitable for use as a contrast agent to form images of biological tissue using optical coherence tomography, light microscopy, holography, confocal microscopy, polarization microscopy, interference microscopy, multi-photon microscopy, and endoscopy.

DETAILED DESCRIPTION

Figure 1:
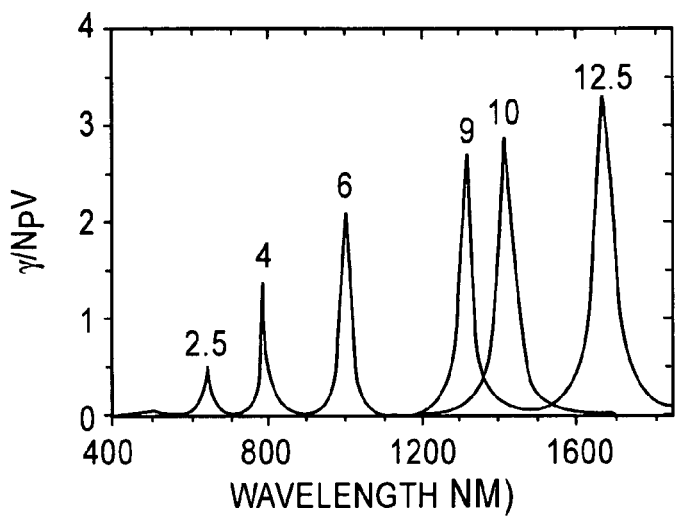
FIG. 1 depicts wavelength specific plasmon-resonances calculated for gold nanorods with the indicated aspect ratios.

The present invention makes use of the discovery that plasmon-resonant nanoparticles can be used to enhance the contrast in analyses and imaging techniques that use electromagnetic radiation, particularly those techniques which use radiation in the frequency range of infrared to ultraviolet, such as optical coherence tomography, light microscopy, holography, confocal microscopy, polarization microscopy, interference microscopy, multi-photon microscopy, and endoscopy. Moreover, metallic nanoparticles composed of gold, silver, and/or copper are particularly suited as contrast agents for OCT applications. Preferably, the nanoparticles are metallic anisotropic nanoparticles, which possess superior plasmon-resonant characteristics and may be fabricated in bimetallic forms to permit their use in OCT applications using switchable magnetic and electric fields. Furthermore, the nanoparticles can be functionalized with biomolecular ligands for cell-specific delivery to permit site-directed OCT imaging. The nanoparticles efficiently absorb the incident optical radiation and can be used as hyperthermia agents, creating local thermal gradients that are sufficient to kill individual cells. These contrast agents can therefore be used simultaneously for the detection and imaging of targeted cells followed by hyperthermic ablation.

A nanosphere represents one form of plasmon-resonant nanoparticle that is useful in the present invention. Preferred nanospheres have diameters of 10 nm to 1 μm. More preferably, the nanospheres have diameters of 20 nm to 500 nm. Even more preferably, the nanospheres have diameters of 40 nm to 200 nm. Methods for the synthesis and modification of nanospheres have been described in the art [88-93, 112].

Colloidal gold nanoparticles are commonly used in biological and biomedical applications because of their inertness under physiological conditions. They are also well known for their intense absorption and scattering properties. Gold nanoparticles functionalized with biomolecular ligands have been employed as carriers and labels in biological tissue staining [51], drug and gene delivery [52-54], and biosensing applications [55]. In this regard, any metallic particle may be coated with gold. The optical responses of colloidal gold particles are enhanced by collective electronic excitations known as surface plasmons, which are responsible for extinction coefficients in the range of $10^9$-$10^{11}$ $M^{-1}$ $cm^{-1}$ [56]. Gold nanoparticles can have anisotropic absorption properties which vary with respect to their orientation relative to the incident optical radiation. Plasmon-resonant nanoparticles can thus be detected at extremely low concentrations, with several orders of magnitude greater sensitivity than organic dye molecules [57]. Furthermore, their optical emissions do not bleach over time and have no saturation limits; in other words, they are optically indefatigable.

Recent activities in nanoscale materials science have further expanded the knowledge base on the optical physics of metallic nanoparticles, and it is now evident that physical structure has a dramatic influence on plasmon-enhanced response. In particular, the optical resonances of anisotropic metallic nanoparticles such as rods, ellipsoids, and triangles have been found to be more intense and frequency-specific than their spherical counterparts, and can be tuned as a function of their size, shape, and interparticle coupling [49, 50]. These variables provide a wealth of opportunities for designing contrast agents with enhanced optical properties at specific wavelengths. Furthermore, metallic anisotropic nanoparticles that possess electromagnetic properties (e.g., bimetallic nanoparticles) permit their use in OCT applications where their orientation can be modulated by either magnetic or electric fields.

Anisotropic nanoparticles of a variety of distinctive shapes are useful as contrast agents in optical coherence tomography. Although preferred embodiments demonstrate the synthesis and utility of metallic nanorods, metallic anisotropic nanoparticles composed of other shapes, like triangles and ellipsoids, may be used. These alternative shapes will yield plasmon-resonant characteristics that are suitable for use as OCT contrast agents and hyperthermic ablation applications.

The general fabrication scheme for preparing other metallic anisotropic nanoparticles differing in shape (e.g., nanotriangles and nanoellipsoids) is an extension of the types of fabrication techniques that are disclosed in the embodiments for metallic nanorods. Nanoporous alumina templates can be prepared that possess unique shapes using controlled etching processes. These templates can then be backplated with metallic Ag, followed by electrodeposition of Au at constant current using a standard gold electroplating solution. Nanoparticles are subsequently released into solution by dissolution of the silica template and recovered by centrifugation. Controlled deposition times can afford anisotropic nanoparticles of various sizes.

Preferably, the nanoparticles are metallic. Preferred metals include gold, silver, copper, cobalt, nickle, iron, and alloys or mixtures thereof. Metallic nanoparticles permit further compositional modification or surface modification of the particles. For example, a compositional modification of a non-magnetic nanosphere (e.g., a gold nanosphere) can be accomplished using cobalt, iron, or nickel to produce particles with magnetic properties. Such magnetic metallic nanoparticles are useful plasmon-resonant contrast agents in applications where OCT is conducted with switchable electric or magnetic fields. Likewise, a surface modification of a metallic nanoparticles (e.g., gold nanoparticles) can be accomplished with small molecules (e.g., crosslinking agents), ligands (e.g., folate) or receptors (e.g., antibodies). Functionalized nanoparticles are useful in the present invention for targeted delivery of nanoparticles to specific cell types (e.g., cancer cells). Furthermore, the nanoparticles may be present as part of a composite. The composite may contain other materials which hold a number of the nanoparticles together, for example ceramics such as alumina, silica or glass; and organic materials such as proteins, lipids, polymers, and carbohydrates.

The development of metallic nanorods as contrast agents imparts several unique parameters for enhancing adsorption or backscattering detection by OCT. First, the nanorods can be optimized for extinction at NIR frequencies as a function of aspect ratio, independently from their diameters; second, the size of their absorption or scattering cross sections can be engineered as a function of unit particle volume; third, the anisotropy of plasmon-enhanced optical response is sensitive to the relative angle of incidence; and fourth, the ability to synthesize bimetallic nanorods allows one to couple plasmon-enhanced optical properties with magnetic properties for novel contrast enhancement.

Surface plasmons in metallic nanoparticles are generated by the collective excitation of free conduction electrons in response to a characteristic optical frequency. An important feature of plasmon resonance is its high sensitivity to shape anisotropy: isolated spherical nanoparticles typically support a single resonance frequency, whereas anisotropic particles (rods, triangles, ellipsoids, etc.) will exhibit at least one additional plasmon mode [56]. In the case of cylindrical nanorods, the frequency of this second (longitudinal) plasmon mode is determined primarily by the particle's aspect ratio, and is redshifted well into the NIR. It has been shown, both theoretically and experimentally, that gold nanorods with aspect ratios of 4:1 exhibit longitudinal plasmon resonances centered at 800 nm, whereas nanorods with aspect ratios of 9:1 exhibit resonances centered at 1.3 μm [49, 50, 58] (see FIG. 1).

Figure 2:
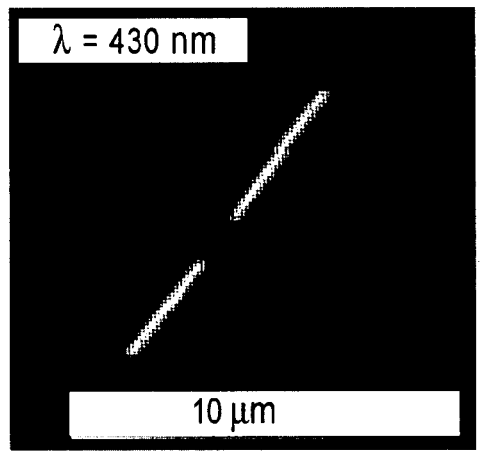
FIG. 2 depicts bimetallic Ag—Au nanorod synthesized by sequential electrodeposition into porous template.

Methodologies for synthesizing metallic nanorods are now well established. Nanoparticle-seeded growth mediated by cationic surfactants can produce cylindrically symmetric nanorods with aspect ratios as high as 20:1, with diameters on the order of 10-20 nm [59, 60]. For thicker nanorods (>20 nm), pulsed electrodeposition into metallized nanoporous membranes has been demonstrated to produce nanorods of nearly every aspect ratio [58, 61, 62]. The latter synthetic method offers excellent control over nanorod dimensions: rod thickness is predetermined by pore diameter, whereas rod length is a direct function of deposition time. In addition, different metals can be deposited sequentially, permitting the synthesis of bimetallic nanorods with dual materials properties (see FIG. 2).

Nanorods can be prepared with preferred aspect ratios of 1.5:1 to 20:1. More preferably, nanorods can be prepared with aspect ratios of 4:1 to 9:1, which display resonant extinction peaks at 800 nm and 1.3 μm, respectively. Nanorods can be prepared with diameters of 10 nm to 300 nm. More preferably, nanorods can be prepared with diameters of 10 nm to 100 nm. The synthesis of metallic nanorods has been optimized by the electrochemical reduction of metallic salts inside nanoporous alumina membranes, as well as by chemical reduction in micellar solutions. The latter method is useful for synthesizing nanorods with diameters of 10 to 20 nm, which can be tuned with a narrow size dispersity by varying the particle seed size, the surfactants comprising the micellar reaction template, or the concentration of associative electrolytes serving as "capping agents" [59, 60]. Electrodeposition can be used to make nanorods of 20 to 300 nm in diameter [58, 61, 62]; in this case, the nanoporous template controls the size and quality of the nanorod dispersions. Individual nanorods of 20 to 40 nm in width have strong absorption and moderate scattering efficiencies, while nanorods of 50-100 nm in diameter have intense NIR scattering cross sections. Transverse plasmon modes also produce strong optical responses in the visible range, regardless of aspect ratio; for example, both nanorods and nanowires (d~30 nm) have been shown to be efficient scattering agents near their transverse plasmon resonance ($\lambda_{max}$~530-580 nm) [63].

Figure 3:
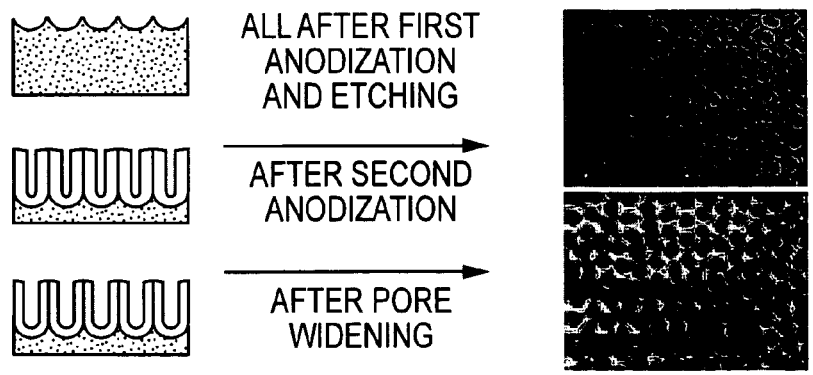
FIG. 3 depicts two-step anodization and pore widening process for nanoporous alumina templates.

It is preferable to obtain nanorods with narrow size dispersity (<10%). With respect to micelle-templated synthesis, the nanorods must be separated and refined by size-selective precipitation or other means of separation. Nanorods can be isolated by size-exclusion techniques assisted by centrifugation, since this technique has been successful in enriching the population of anisotropic nanoparticle oligomers [64]. With respect to electrochemical synthesis, it is essential to produce nanoporous templates of high quality in order to obtain nanorods of narrow size dispersity. Commercially available alumina membranes often have nonuniform or poorly defined pore sizes; therefore, one can prepare nanoporous membranes with customized diameters by anodizing high-grade aluminum (99.9999%, PVD Materials) under well-defined conditions. Highly uniform nanoporous alumina can be prepared by a two-step anodization process: (1) a sacrificial oxide layer is first formed and removed by hydrolysis, leaving behind a periodically dimpled surface; (2) a second anodization produces a periodic array of nanopores, whose diameters are determined by the applied voltage [65-67]. The pores can also be further enlarged by acid-assisted electrochemical etching [68]. This process has been used to prepare alumina membranes with 60- and 90-nm pores (see FIG. 3).

These and other methods for preparing nanorods are available to one of ordinary skill in the art and have been described in the literature [59-63, 69, 70]. Likewise, general procedures for the preparation of nanotriangles are disclosed in the literature [71-73].

Biomolecular ligands can be conjugated onto colloidal particles by simple electrostatic adsorption [51]. Protein-conjugated nanoparticles can also be internalized by receptor-mediated endocytosis [74-78], thereby providing a useful mechanism for cell uptake. Electron microscopy studies demonstrate that nanoparticle uptake correlates strongly with ligand-induced receptor clustering [79, 80], and that the conjugated proteins are densely packed on the particle surface [81]. These have obvious applications for site-directed OCT imaging as well as for localized hyperthermia.

Nanoparticles have also been functionalized with small-molecule ligands, most notably by the spontaneous chemisorption of thiols onto gold or gold-coated nanoparticles [82]. However, the adsorption of thiolated ligands is reversible and results in facile surface exchange. In other embodiments, surface functionalization of gold nanoparticles can be achieved through chemical modification [82-94] and through use of biomolecule ligands [74-81, 95]. The methods for coating metallic nanoparticles in chemically robust, long-lived shells, some of which are amenable to chemical functionalization, are generally available to one skilled in the art [88-93].

Passivating organic surfactants such as n-alkanethiols have been widely used to functionalize and disperse metallic nanoparticles. However, such surfactants are prone to surface exchange, which limits their robustness as ligands for biological applications. The dispersion and functionalization of colloidal metallic nanoparticles in the 10-200 nm range are accomplished by developing surfactants from a class of macrocycles known as resorcinarenes [84-86, 96-98]. These compounds possess large, multivalent headgroups for robust adsorption onto nanoparticle surfaces, and several hydrocarbon tails per molecule spaced several angstroms apart (see FIG. 4). The hydrocarbon tails ensure a high degree of configurational freedom per chain in the surfactant layer, which translates into effective dispersion control.

Figure 4:
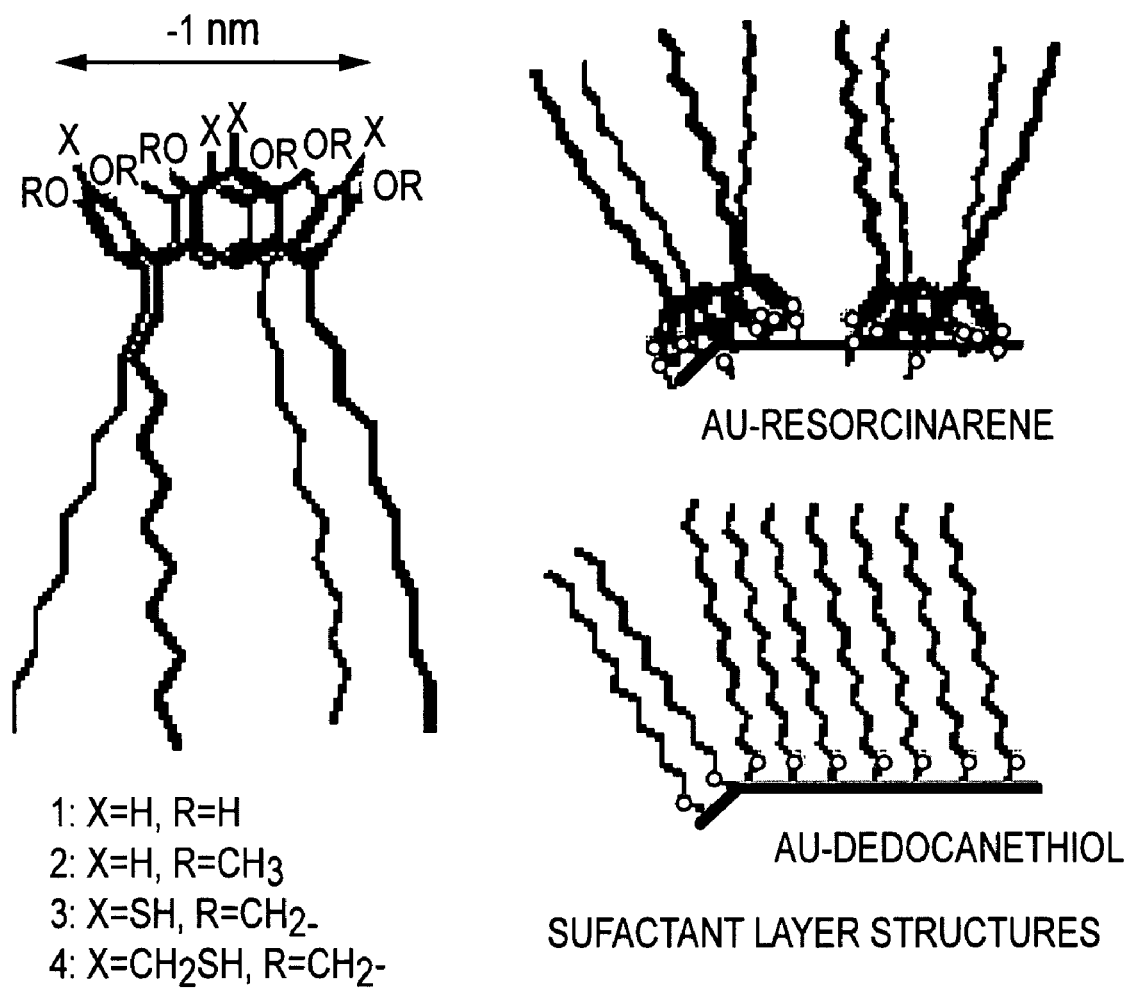
FIG. 4 depicts resorcinarenes as nanoparticle dispersants.

Dispersion studies have been performed using Au nanoclusters encapsulated by resorcinarenes with polyoxygenated headgroups (see FIG. 4, compounds 1 and 2) [84, 98] and by resorcinarenes with tetrathiol headgroups (see FIG. 4, compounds 3 and 4). The latter are able to extract colloidal Au particles as large as 100 nm from aqueous suspensions and disperse them into organic solvents for further chemical functionalization [85, 86]. Preferred nanoparticles include those that are encapsulated by compounds 3 or 4, as they are highly resistant to surface exchange, and are capable of resisting degradation by competing surfactants and other adsorbates over a period of several weeks.

These and other techniques for dispersing nanoparticles using resorcinarenes are described in U.S. patent application Ser. No. 10/218,185 entitled "NANOPARTICLE ARRAYS AND SENSORS USING SAME," to Alexander Wei et al., filed on Aug. 12, 2002 and published Apr. 10, 2003, the contents of which are hereby incorporated by reference.

Optical hyperthermia can be induced at both visible and NIR wavelengths. Fully noninvasive optical hyperthermia is possible if two criteria can be met: (1) a mechanism for site-specific energy delivery to the target area with minimal collateral damage, and (2) energy transport such that the intervening tissue is not subject to thermal heating. The latter can be achieved using ultrashort laser pulses, which deliver coherent light to tightly confined focal regions in high-energy bursts. By concentrating the laser energy into a train of high-peak-power pulses, the average power can be decreased and collateral heating of surrounding tissue can be minimized. This effect has been studied in retinal tissue, in which linear increases in pulse power produced nonlinear increases in tissue damage [99-101]. By developing nanoparticles with high NIR responses as site-directed multifunctional agents, the primary function of OCT as an imaging technology is thereby extended to yield a complementary therapeutic technique.

OCT has been applied toward image-guided laser ablation of surgical tissue in vitro [102]. Laser-induced hyperthermia was performed using a high-power argon laser (514 nm) to thermally coagulate blood within two vessels, located 1.5 mm deep in muscle tissue. Coagulation within the blood vessels (0.0-0.5 sec) occurred prior to overlying tissue damage, due the high absorption coefficient of blood at 514 nm. The image sequence demonstrates OCT monitoring of the process in real time, providing feedback to the surgeon. In this case, optical imaging and laser-induced hyperthermia were performed using two separate instruments. Optionally, OCT with variable incident optical power can be used in conjunction with NIR-resonant nanorods for in vivo targeting and noninvasive destruction of cells deep within tissue.

EXAMPLES

Example 1

Synthesis of Gold Nanorods

Figure 5A:
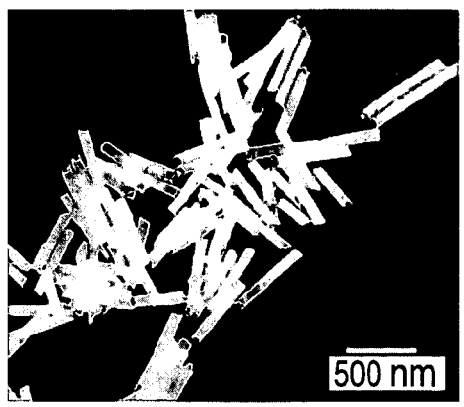
FIGS. 5A and 5B depict Au nanorods prepared by electrodeposition (width: 75 nm; aspect ratio: 10:1 and 4:1, respectively)
Figure 5B:
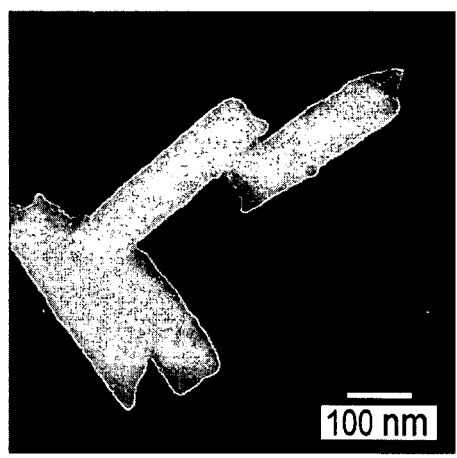
Figure 5C:
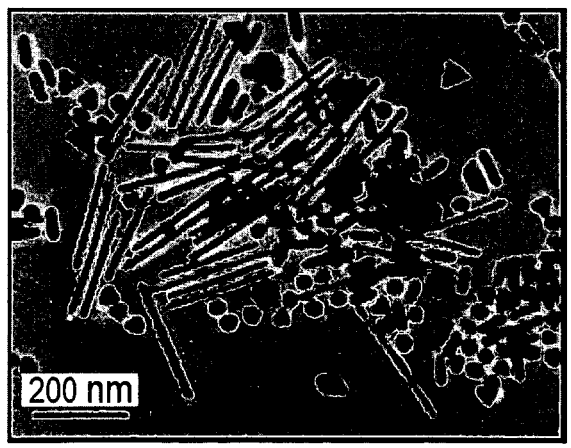
FIG. 5C depicts Au nanorods prepared by chemical reduction (width: 25 nm; aspect ratio: 10:1)

Commercially available nanoporous alumina templates (Anodisc membranes, Whatman) were backplated with metallic Ag, followed by electrodeposition of Au at constant current (0.6 mA/cm$^2$) using a standard gold electroplating solution (Technics, Inc.). Nanorods were released into solution by dissolution of the alumina template and recovered by centrifugation. Controlled deposition times afforded nanorods of various aspect ratios ranging from 4:1 to 10:1 (see FIG. 5A,B). The optical properties of these nanorods extend well into the NIR, and can be tuned for extinction at precise wavelengths as a function of aspect ratio. We have also prepared gold nanorods with much narrower widths by surfactant-mediated synthesis in aqueous solutions. Small (3-4 nm) gold particles were used to nucleate the reduction of gold chloride by ascorbic acid in the presence of cetyltrimethylammonium bromide, following the protocol of Murphy and coworkers [60]. The aspect ratio of the gold nanorods was controlled by adjusting the seed solution amount; in the example above, nanorods were produced with an aspect ratio of about 10:1 (see FIG. 5C).

Example 2

Optical Characterization of Tissue Models

Tissue models consisting of a mixture of dyes for absorption, polystyrene latex microspheres for scattering (Bangs Laboratories), and agarose gelatin for structural support (Sigma Chemicals) will be constructed to simulate the optical characteristics of different tissues [103]. Absorption and scattering coefficients can be independently controlled to represent various tissue types. Absorption properties may be modified by the addition of mixtures of FD&C Yellow #5 and FD&C Blue #1. These dyes increase absorption preferentially in the 630-700 nm region of the optical spectrum. Although the addition of these dyes will simulate tissue optical properties, they have minimal interference with OCT imaging which will be performed at NIR wavelengths (800-1300 nm). Therefore, imaging characteristics will be strongly dependent on the scattering properties of the tissue model versus the absorption properties. Scattering properties can be easily adjusted by varying the concentration and size of polystyrene microspheres [103].

Nanorods may be incorporated into the tissue model in a variety of ways. The optical contrast agents may be added in as layers at varying concentrations and depths. Optionally, the nanorods may be suspended in a liquid solution and drawn up into a 1-cc syringe with a 28-gauge needle in order to introduce contrast agents into a spatially localized region. This may be positioned over the tissue model using a 3-axis micromanipulator stage, enabling contrast agents to be injected at a precise location. The absorption and scattering properties of tissue models may be determined with and without the addition of optical contrast agents using oblique-incidence optical fiber reflectometry [104, 105]. This technique is a simple and reliable method that can be readily incorporated into the OCT instrument and used for tissue models, in vitro cell cultures, and in vivo tissues.

The absorption and reduced scattering coefficients of the sample can be determined by viewing the OCT imaging beam on the surface of the sample or specimen with a CCD camera sensitive to NIR wavelengths (Princeton Instruments). Prior to OCT imaging, the tissue model or in vivo specimen may be placed on the OCT instrument stage so that the incident beam is at a known oblique angle. The CCD camera will capture the diffuse reflectance pattern of the OCT beam on the sample or specimen. From this image, one can determine the distance between the point of incidence and the apparent center of diffuse reflectance. Using this measurement and the known angle of incidence, the absorption and reduced scattering coefficients can be calculated [104, 105]. For tissue models or in vivo specimens that have localized regions of contrast agents, two-dimensional (2D) maps may be generated to represent the spatial distribution of the optical properties (absorption and reduced scattering coefficients). Maps may be generated by stepping the position of the sample or specimen using computer-controlled stages, repeatedly capturing CCD images and calculating the optical properties.

Example 3

Synthesis of Magnetically Tipped Nanorods

Plasmon-resonant nanorods appended with magnetic tips may be synthesized by sequential electrodeposition of Au and Ni in nanoporous alumina templates, as previously described [62]. Ni is preferred for several reasons: first, it can be electrodeposited at low voltages; second, its high magnetic shape anisotropy and low crystalline anisotropy make it easy to predict and control nanorod orientation in an applied magnetic or electric field; and third, it forms a stable, hydrophilic oxide shell which is resistant to degradation under physiological conditions. Although Ni is less desirable from a toxicological perspective, the amounts involved are submicrogram in quantity, and other magnetic materials can be used. One may prepare Au/Ni nanorods with a [4+2]:1 aspect ratio; the Au segment will be resonant at 800 nm, and the Ni segment exhibit a uniaxial magnetic dipole. Although Ni and Au can be deposited in either order, unreduced metal salts from the first deposition residing in the pores can affect the final composition; therefore, TEM analysis may be used for accurate structural characterization.

Example 4

Oriented and Dynamic Optical Response of Magnetically and Electrically Active Nanorods (Prophetic Example)

The modulation of the optical responses of the bimetallic Au/Ni nanorods will be evaluated using applied magnetic fields for orientation effects, at both constant and time-modulated (dynamic) field strengths. Using the solenoid integrated with a microscope, a static magnetic field will be applied to the tissue model with the magnetic field vector aligned either at 0° or 180° with respect to the direction of the incident optical beam. This will cause the polar magnetic nanorods to align with the magnetic field and change the optical scattering and absorption properties compared to the randomly oriented state. Quantitative measurements will be made, along with measurements from field orientations in the range of 0° to 180° to determine the relative backscatter and absorption properties of the nanorods with respect to orientation angle. These physical measurements will help one skilled in the art to develop a better understanding of the novel magneto-optical contrast mechanisms observed so far and a rational basis for further optimization.

In a similar manner, the electric dipoles of the magnetic bimetallic particles will be oriented as a function of electric field strength in switchable electric fields.

Example 5

In Vitro Optical Modulation by Magnetic Particles (Prophetic Example)

Magnetic particles confined within intracellular compartments will be detected optically under externally applied fields. Macrophages (ATCC #TIB-67) will be cultured overnight in the presence of three forms of magnetic colloids or suspensions, which were internalized by phagocytosis. The samples that will be studied include: (1) ferromagnetic hematite ($Fe_2O_3$) nanoparticles aggregated into micron-sized clusters suspended in phosphate-buffered saline (PBS), (2) superparamagnetic magnetite ($Fe_3O_4$) colloid, and (3) superparamagnetic latex beads (40% magnetite+60% divinylbenzene; 2.38 μm in diameter) suspended in PBS. Cell counts after incubation for 48 hours should indicate healthy cultures for all samples. Dishes containing the magnetically labeled macrophages will then placed atop a solenoid coil on a bright-field microscope, and monitored with a water-immersion objective under an applied magnetic field (~300 G). The corresponding gradient in the axial direction should be estimated to be ~6 T/m at the dish surface.

Cells containing the magnetic nanoparticles will be monitored under both constant and fluctuating magnetic fields. Intracellular movement should be detectable with particles (1) but not with particles (2) or (3), suggesting that ferromagnetic behavior was important for this form of contrast. Translational movement of the hematite nanoparticles will be monitored in both the axial and transverse directions; rotational alignment of the particles will also be monitored as the magnetic field was switched on.

Example 6

Functionalization of Nanorods with Bioreceptors (Antibodies) (Prophetic Example)

The cell-surface folate receptor will be chosen as a target for nanorod labeling and OCT contrast detection. Nanorod agents will be functionalized using monoclonal antibodies raised against folate receptors (human folate receptor a: MOV18/ZEL, Alexis Biochemicals; folate-binding protein: ab2107, abcam) as well as the folate ligand itself (see below). Methods for conjugating antibodies onto colloidal gold nanoparticles ("ImmunoGold") are well-established and will be applied toward nanorod contrast agents [51]. The antibody-conjugated nanorods will be typically suspended at a concentration of $10^{10}$ particles/mL, and administered in vivo for site-directed labeling of carcinoma cells in the hamster cheek pouch model (see below).

Example 7

Functionalization and Coating Methodologies for Ligand-Conjugated Nanorods (Folates) (Prophetic Example)

Nanorods will be encapsulated in crosslinked surfactant layers. This surface is ideal for grafting complex organic ligands such as folate using olefin cross-metathesis [106, 107]. Encapsulated nanorods will be isolated from excess surfactant by centrifugation, then resuspended and treated with $Cl_2(Cy_3P)_2Ru$=CHPh at sub-millimolar concentrations. These will be centrifuged again and redispersed in the presence of allyl folate ester. Ru-catalyzed olefin metathesis is a well-known "living" polymerization method, and is tolerant of an enormously diverse range of functional groups and reaction conditions [108]. Some of the catalytic Ru will be covalently tethered to the nanorod surfactant layer, with additional coordination by nearby crosslinked cis-olefins. These cis-olefins are capable of further metathesis with the Ru catalyst, so that the degree of intermolecular crosslinking within the resorcinarene monolayer ("annealing") will gradually increase over time. A modification of this approach will permit the addition of allyl folate to the Ru-conjugated nanorods without removing excess Ru catalyst to yield Ru=alloxylidene folate at submillimolar concentrations. These will undergo cross-metathesis with cis-olefins in the crosslinked shell to yield folate-labeled nanorods with high surface coverage.

Example 8

Nanoparticles Stabilized by Cross-Linked Surfactant Shells

Figure 6:
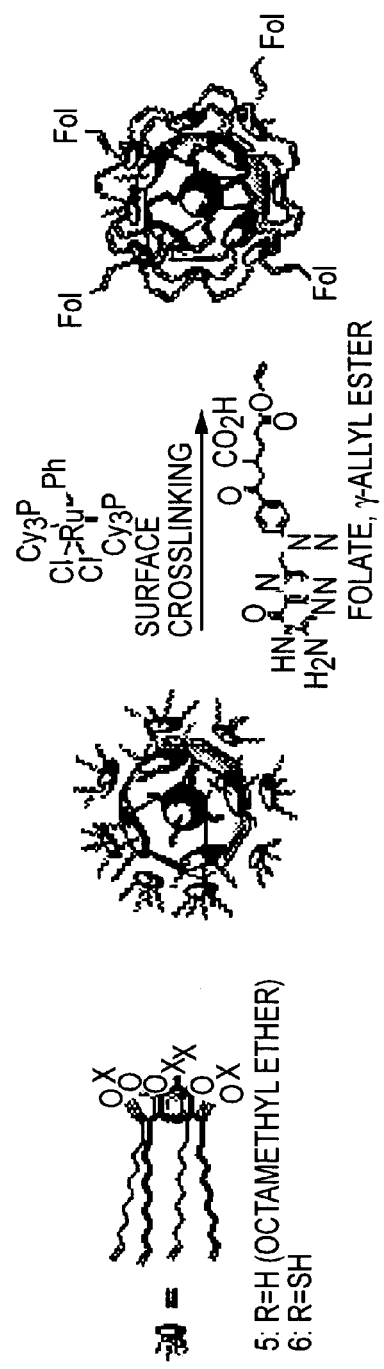
FIG. 6 depicts ligand-functionalized nanoparticles via tandem surfactant cross-linking/ligand cross-metathesis (folate is denoted as "Fol")

Resorcinarene-encapsulated nanoparticles are robust ligand-directed agents for imaging and therapeutic applications. While surfactants bearing substituents 3 and 4 have superior resistance against desorption, long-term stability and chemical erosion remain critical issues for biological applications. To overcome these issues, a surface polymerization protocol was developed that crosslinks resorcinarene surfactant layers into robust yet functional coatings (see FIG. 6). Nanoparticles are encapsulated by surfactants with terminal alkenes such as substituents 5 and 6, which can be crosslinked by olefin metathesis using $Cl_2(Cy_3P)_2Ru=CHPh$, a ruthenium carbene catalyst introduced by Grubbs [106, 107]. The resorcinarene coatings are sufficiently dense to allow for significant intermolecular cross-linking, thereby yielding a nondesorptive surfactant monolayer. The cross-linked shells are capable of further metathesis with alkene-bearing molecular ligands, so that their covalent attachment is irreversible.

Figure 7:
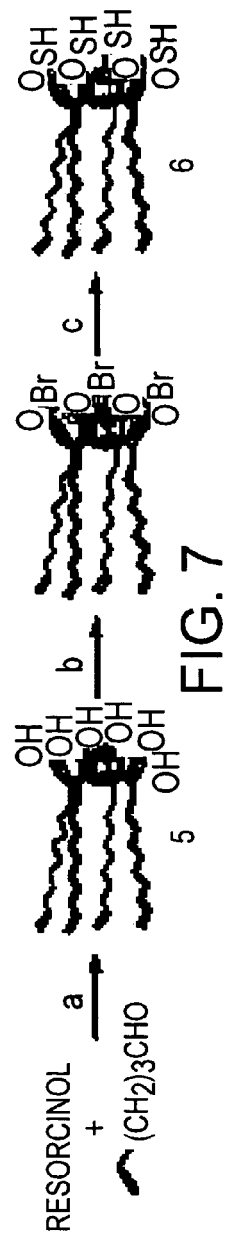
FIG. 7 depicts a synthetic scheme of resorcinarenes bearing substituents 5 and 6.

A test study was conducted using Au nanoclusters encapsulated by resorcinarene tetraolefin substituent 5 [109]. Kinetic studies on the intramolecular metathesis of 5 by $Cl_2(Cy_3P)_2Ru=CHPh$ using $^1H$ NMR spectroscopy provided effective first-order rate constants at different catalyst loadings and reactant concentrations, which suggested reaction conditions for producing surfactant layers with a high degree of crosslinking. Dispersions of encapsulated Au nanoclusters treated in this manner were indeed found to be highly robust; however, nanoparticles encapsulated in highly crosslinked shells were poorly dispersible because of the loss of surfactant chain mobility, which limited their processing potential. A second-generation system based on tetrathiol-tetraolefin substituent 6 has been developed, in which strong chemisorption and olefin metathesis operate synergistically to produce highly robust but dispersible encapsulated nanoparticles. Resorcinarene bearing substituent 6 was synthesized according to FIG. 7 ((a) HCl, EtOH, 65° C. (70% yield); (b) i) N-bromosuccinamide, 2-butanone; ii) $CH_2BrCl$, $Cs_2CO_3$, DMF, 100° C. (40% yield over 2 steps); (c) n-BuLi, THF, −78° C. to 0° C. (85% yield)) and used to extract 20-nm colloidal Au particles from aqueous solutions into toluene. Cross-linking was performed by treating nanoparticle suspensions with Ru metathesis catalyst for 5 minutes ($5 \times 10^{11}$ particles/mL, or ~1 pM), then quenching with ethyl vinyl ether. Tetrathiol substituent 6 did not have a negative impact on the catalyst's activity, such that cross-linking could be performed in the presence of excess surfactant.

For these and other techniques for dispersing nanoparticles using resorcinarenes, see U.S. patent application Ser. No. 10/218,185 entitled "NANOPARTICLE ARRAYS AND SENSORS USING SAME," to Alexander Wei et al., filed on Aug. 12, 2002 and published Apr. 10, 2003.

The robustness of the cross-linked surfactant shells can be evaluated by exposing the nanoparticle dispersions to dodecanethiol, a strongly adsorbing surfactant with poor dispersant properties. All resorcinarene-stabilized dispersions were observed to be stable after a one-week exposure to dodecanethiol at room temperature; however, those which were not subjected to metathesis-mediated crosslinking degraded within a few hours at 70° C. Nanoparticle dispersions treated with 0.01 mM catalyst or less were also degraded within a few hours, but nanoparticles treated with 0.1 mM catalyst were found to be completely stable under these conditions. Nanoparticles stabilized in cross-linked surfactant layers could also be repeatedly precipitated by centrifugation and redispersed by mild sonication with high levels of recovery.

These experiments demonstrate that shells of cross-linked 6 can be highly resistant to surface desorption, while retaining excellent dispersibility in various solvents for subsequent funtionalization. Transmission electron microscopy (TEM) provides further evidence correlating dispersion stability with metathesis cross-linking; uncross-linked nanoparticles precipitated by dodecanethiol were redispersed and cast onto Formvar-coated TEM grids, and were observed to have formed aggregates. Nanoparticle dispersions treated with low catalyst loadings produced mixtures of monodispersed and aggregated particles, whereas dispersions treated with high catalyst loadings were completely redispersed.

Example 9

Functionalization of Crosslinked Nanoparticle Shells

Figure 8:
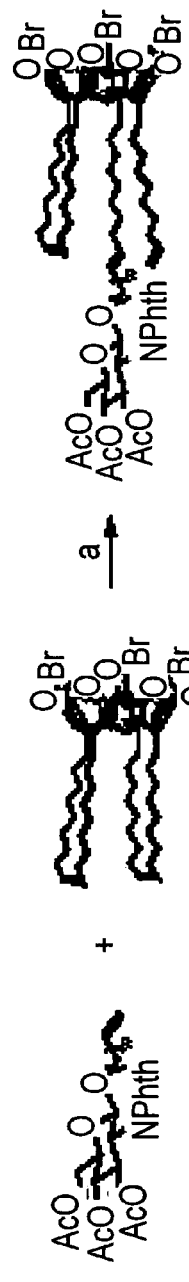
FIG. 8 depicts a synthetic scheme of cross-metathesis of ligand onto cross-linked surfactant model.

Nanoparticles stabilized in monolayer shells of 6 were treated with Ru metathesis catalyst, then centrifuged without quenching and redispersed in fresh solvent containing polymerizable norbornene derivatives or alkene-bearing ligands. An inverse approach to cross-metathesis-crosslinking may be used wherein which the Ru catalyst is first treated with an alkenyl ligand such as substituent 7a or 7b (see FIG. 8 ("NPhth" denotes phthalimide, (a) 7a or 7b (1 equivalent), $Cl_2(Cy_3P)_2Ru=CHPh$ (1 equivalent), tetrabromoresorcinarene cis-deine (2 equivalents), toluene)). Cross-metathesis of the resulting Ru=alkylidene intermediate with resorcinarene cis-diene substituent 8 (a model compound for the crosslinked surfactant layer) produces a 1:1 adduct in significant quantities along with some doubly functionalized resorcinarene; the cross-coupling reaction between substituents 7b and 8 proceeds in similar fashion. These reactions are the molecular analogy to the proposed surface functionalization, and support the notion that alkenyl ligands can be reliably grafted onto the crosslinked surfactant layer.

Example 10

Evaluation of Anisotropic Nanoparticle Uptake by Cells In Vitro and Intracellular Nanorod Aggregation (Prophetic Example)

Site-directed nanorod labeling and possible cell uptake will be evaluated with in vitro cultures of KB tumor cells, which express high levels of folate receptor on their surfaces [110]. For example, cells will be plated and exposed to antibody- and folate-conjugated nanorods at femtomolar to low picomolar concentrations to establish their relative affinity of binding. Cell labeling will be characterized first by OCT imaging, then by cryo-electron microscopy and by a standard silver-staining histological protocol [51]. Antibody-labeled nanorods should bind to the exterior of KB cells, whereas folate-labeled nanorods should be taken up by receptor-mediated endocytosis (cf. FIG. 3a). This will provide an important variable in optical contrast generation, as the latter nanorods exist in an aggregated state. Differences in optical contrast quality will determine whether antibody-labeled nanorods are preferred over folate-labeled nanorods, or vice versa.

Example 11

In Vivo OCT Imaging of Hamster Cheek Pouch Tumors Using Folate-Labeled Nanorods (Prophetic Example)

The Syrian Golden hamster cheek pouch carcinogenesis model closely resembles the events involved in the development of premalignant and malignant human oral cancers [108, 110, 111]. This is a well-characterized model for squamous cell carcinoma, which is the leading form of malignancy in human skin, oral, and genital mucosas. The cheek pouch model is ideal for imaging and contrast localization studies on pre-malignant through metastatic stages.

Syrian Golden hamsters (100 to 120 g) will have cotton sutures inserted submucosally into both cheek pouches under intraperitoneal anesthetics (pentobarbital sodium, 500 mg/kg). A 0.5% solution of 9,10-dimethyl-1,2-benzanthracene (DMBA, Sigma Chemical) will be painted on the left cheek pouches biweekly, starting 4 weeks after the sutures are placed; the right cheek pouch will serve as the normal control. Imaging of tumor sites in the hamster cheek pouch will take place weekly, beginning at 10 weeks after tumor induction and while the tumors are at early pre-malignant stages. At early stages, abnormal dysplastic cells are likely to be present before changes can be observed visually. Four animals will be imaged each week; prior to imaging, animals will be anesthetized with intraperitoneal anesthetics (pentobarbital sodium, 500 mg/kg). The cheek pouch will be everted and the animal will be positioned on the instrument stage under the OCT imaging beam. Following CCD image collection to measure the optical properties of the in vivo tissue, 3D OCT imaging will be performed at the site indicated by the suture. Both the left (tumor site) and the right (control site) cheek pouches will be imaged. Subsequently, a solution of freshly suspended functionalized nanorods (~$10^{10}$ nanorods/µL) will be injected intravenously via a tongue vein. Doses will range of 5 µL to 100 µL, depending on the efficiency of uptake by the neoplastic cells.

Thirty minutes following injection, 3D optical property measurements and OCT imaging will be repeated for both cheek pouches. If magneto-optical contrast mechanisms are to be employed, then animals will be positioned on the OCT imaging stage with the solenoid positioned over the tumor sites to orient the magnetic nanorods at varying angles relative to incident optical radiation. OCT imaging will be performed in different experiments at 800 nm and 1.3 µm, and for varying magnetic field orientations (0° to 180° with 10° increments). For each series of experiments, real-time structural and spectroscopic OCT imaging will be used to detect changes in the scattering and absorption properties of the tissue. Correlations will be made between the 2D maps of optical properties and the 3D OCT images. Additionally, measurements from OCT images will characterize the enhancement in tumor detection by the contrast agent.

At the conclusion of each weekly imaging experiment, one of the animals will be allowed to recover. The three remaining animals will be euthanized by $CO_2$ inhalation, and tissue from the cheek pouches will be excised for histopathological observations using light, confocal, and electron microscopy. Microscopy findings of tumor morphology and contrast agent localization will be correlated with the OCT image findings to determine specific OCT image features that indicate the presence of the nanorod contrast agents.

Example 12

Optical Hyperthermia on Tissue Phantoms with Real-Time OCT Monitoring (Prophetic Example)

Optical hyperthermia studies will be performed in tissue models with and without plasmon-resonant contrast agents. Structural and spectroscopic OCT imaging of tissue models will be performed using low (5 mW) optical power using optimized sampling configurations and contrast mechanisms. OCT will then be performed using incrementally larger optical powers (5 mW steps, up to 50 mW) while observing for signs of hyperthermia-induced changes in real time. In case the lowest incident power is still too high, off-resonant nanorods with different aspect ratios will be used to attenuate their plasmonic responses. Imaging exposure time of the tissue model will initially be 1 minute at each optical power level, and will be varied from 1 to 5 minutes to determine exposure thresholds for hyperthermia-induced changes. Using OCT, changes are likely to include local increases in optical backscatter and structural changes in the tissue model. Due to the presence of the highly absorbing nanorods, local hyperthermia effects should coincide with the spatial distribution of the nanorods as detected using OCT. Simultaneously with real-time OCT imaging, one may record local temperature changes within the tissue model using a miniature thermistor embedded within the agarose layers of a tissue model and record surface and bulk temperature changes using a temperature-calibrated infrared camera. Following each imaging session, the tissue model will be physically sectioned along the OCT imaging plane using a razor blade and placed on a glass microscope slide for high-resolution light microscopy of the imaging site. Digital light microscopy will be used to verify the presence or absence of any local hyperthermia effects. These images may be compared with structural and spectroscopic OCT images to determine the threshold at which OCT can detect the onset of hyperthermia.

Example 13

Nanoparticle-Assisted Optical Hyperthermia In Vivo (Prophetic Example)

Optically-induced hyperthermia data obtained from the tissue model studies will serve as a guide for inducing hyperthermia in vivo in animal tumor models. Nanoparticles with folate ligands will be injected intravenously into the tongue vein of an anesthetized hamster with squamous cell carcinomas present in the cheek pouch as previously described. Thirty minutes following injection, animals will be positioned on the OCT imaging stage under optimized imaging configurations. OCT imaging will be performed at 800 nm and 1.3 µm for varying exposure durations (1-5 min at 1-min increments) and optical powers (5-50 mW at 5-mW increments). For each series of experiments, real-time OCT imaging will be used to monitor hyperthermia-induced changes in depth, and infrared camera imaging will be used to detect hyperthermia-induced changes at the surface. Changes indicative of hyperthermia-induced injury include increased optical backscatter or absorption in microstructural or spectroscopic OCT, and changes in the birefringent properties of the tissue (most notably light-dark banding in OCT images from ordered muscle fibers).

Example 14

Fabrication of Microparticles with a Gold Coat

BSA is also known to interact very strongly with gold nanoparticles via its amine and thiol residues [113]. Because of the presence of thiol and amine groups, the microparticle can be used as a template for the adhesion of gold nanoparticles. Addition of positive polymer layer was not performed for adhesion of the gold colloid unto the surface of the microparticle. The gold colloid can adsorb directly onto the protein shell via interaction with thiol and amine groups [113]. The red colloidal gold solution used in this synthesis was prepared via the reduction of chloroauric acid in the presence of sodium citrate [114]. The milky white solution of oil-filled microparticle generated from sonication was poured into a equal amount of the red colloidal gold solution. The mixture was shaken gently for 25 min and allowed to phase separate. Following phase separation, the supernatant took on a reddish color; an indication that the gold particles had been transferred to the microparticles. These microparticles were centrifuge-washed twice and still retained their reddish color.

REFERENCES

1. Christiansen C, Kryvi H, Sontum P C, Skotland T. Physical and biochemical characterization of Albunex, a new ultrasound contrast agent consisting of air-filled albumin microparticles suspended in a solution of human albumin. Biotechnol. Appl. Biochem. 19:307-20, 1994.
2. Gazelle G S, Wolf G L, McIntire G L, Bacon E R, Halpern E F, Cooper E R, Toner J L. Nanoparticulate computed tomography contrast agents for blood pool and liver-spleen imaging, Acad. Radiol. 1:373-76, 1994.
3. Su M Y, Muhler A, Lao X, Nalcioglu O. Tumor characterization with dynamic contrast-enhanced MRI using MR contrast agents of various molecular weights, Magn. Reson. Med. 39:259-69, 1998.
4. Bugaj J E, Achilefu S, Dorshow R B, Rajagopalan R. Novel fluorescent contrast agents for optical imaging of in vivo tumors based on a receptor-targeted dye-peptide conjugate platform, J. Biomed. Opt. 6:122-33, 2001.
5. Huang D, Swanson E A, Lin C P, Schuman J S, Stinson W G, Chang W, Hee M R, Flotte T, Gregory K, Puliafito C A, Fujimoto J G. Optical Coherence Tomography. Science 254: 1178-81, 1991.
6. Fujimoto J G, Brezinski M E, Tearney G J, Boppart S A, Bouma B E, Hee M R, Southern J F, Swanson E A. Biomedical imaging and optical biopsy using optical coherence tomography. Nature Medicine 1:970-72, 1995.
7. Brezinski M E, Tearney G J, Bouma B E, Izatt J A, Hee M R, Swanson E A, Southern J F, Fujimoto J G. Optical coherence tomography for optical biopsy: properties and demonstration of vascular pathology. Circulation 93:1206-13, 1996.
8. Schmitt J M, Knuttel A, Bonner R F. Measurements of optical properties of biological tissues by low-coherence reflectometry. Appl. Opt. 32:6032-42, 1993.
9. Sergeev A M, Gelikonov V M, Gelikonov G V, Feldchtein F I, Kuranov R V, Gladkova N D, Shakhova N M, Snopova L B, Shakov A V, Kuznetzova I A, Denisenko A N, Pochinko V V, Chumakov Y P, Streltzova O S. In vivo endoscopic OCT imaging of precancer and cancer states of human mucosa. Opt Express 1:432-40, 1997.
10. Tearney G J, Brezinski M E, Bouma B E, Boppart S A, Pitris C, Southern J F, Fujimoto J G. In vivo endoscopic optical biopsy with optical coherence tomography. Science. 276:2037-39, 1997.
11. Boppart S A, Bouma B E, Pitris C, Tearney G J, Southern J F, Brezinski M E, Fujimoto J G. Intraoperative assessment of microsurgery with three-dimensional optical coherence tomography. Radiology. 208:81-86, 1998.
12. Morgner U, Drexler W, Kartner F X, Li X D, Pitris C, Ippen E P, Fujimoto J G. Spectrosopic optical coherence tomography. Opt. Lett., 25:111-13, 2000.
13. Leitgeb, R., Wojtkowski, M., Kowalczyk, A., Hitzenberger, C. K., Sticker, M., and Fercher, A. F. Spectral measurement of absorption by spectroscopic frequency-domain optical coherence tomography. Opt. Lett. 25:820-22, 2000.
14. Chen Z, Milner T E, Srinivas S, Wang X. Noninvasive imaging of in vivo blood flow velocity using optical Doppler tomography. Opt. Lett. 22:1119-21, 1997.
15. Yazdanfar S, Kulkarni M D, Izatt J A. High resolution imaging of in vivo cardiac dynamics using color Doppler optical coherence tomography. Opt. Express. 1:424-31, 1997.
16. Hee M R, Izatt J A, Swanson E A, Huang D, Schuman J S, Lin C P, Puliafito C A, Fujimoto J G. Optical coherence tomography of the human retina. Arch. Ophthalmol. 113: 325-32, 1995.
17. Puliafito C A, Hee M R, Lin C P, Reichel E, Schuman J S, Duker J S, Izatt J A, Swanson E A, Fujimoto J G. Imaging of macular disease with optical coherence tomography (OCT). Ophthalmology 102:217-29, 1995.
18. Puliafito C A, Hee M R, Schuman J S, Fujimoto J G. *Optical Coherence Tomography of Ocular Diseases*. Slack, Inc, Thorofare, N.J., 1995.
19. Schmitt J M, Knuttel A, Yadlowsky M, Eckhaus A A. Optical coherence tomography of a dense tissue: statistics of attenuation and backscattering. Phys. Med. Biol. 39:1705-20, 1994.
20. Schmitt J M, Yadlowsky M J, Bonner R F. Subsurface imaging of living skin with optical coherence microscopy. Dermatology 191:93-98, 1995.
21. Profio A E, Doiron D R. Transport of light in tissue in photodynamic therapy of cancer. Photochem. Photobiol. 46:591-99, 1987.
22. Tearney G J, Brezinski M E, Boppart S A, Bouma B E, Weissman N, Southern J F, Swanson E A, Fujimoto J G. Catheter-based optical imaging of a human coronary artery. Circulation 94:3013, 1996.
23. Tearney G J, Brezinski M E, Southern J F, Bouma B E, Boppart S A, Fujimoto J G. Optical biopsy in human gastrointestinal tissue using optical coherence tomography. Amer. J. Gastroenterol. 92:1800-04, 1997.
24. Tearney G J, Brezinski M E, Southern J F, Bouma B E, Boppart S A, Fujimoto J G. Optical biopsy in human urologic tissue using optical coherence tomography. J. Urol. 157:1915-19, 1997.
25. Boppart S A, Brezinski M E, Pitris C, Fujimoto J G. Optical Coherence Tomography for Neurosurgical Imaging of Human Intracortical Melanoma. Neurosurgery 43:834-41, 1998.
26. Bouma B E, Tearney G J, Boppart S A, Hee M R, Brezinski M E, Fujimoto J G. High resolution optical coherence tomographic imaging using a modelocked $Ti:Al_2O_3$ laser. Opt. Lett. 20:1486-88, 1995.
27. Drexler W, Morgner U, Kartner F X, Pitris C, Boppart S A, Li X, Ippen E P, Fujimoto J G. In vivo ultrahigh resolution optical coherence tomography. Opt. Lett. 24:1221-23, 1999.
28. Tearney G J, Bouma B E, Boppart S A, Golubovic B, Swanson E A, Fujimoto J G. Rapid acquisition of in vivo biological images using optical coherence tomography. Opt. Lett. 21:1408-10, 1996.
29. Tearney G J, Boppart S A, Bouma B E, Brezinski M E, Weissman N J, Southern J F, Fujimoto J G. Scanning single-mode fiber optic catheter-endoscope for optical coherence tomography. Opt. Lett. 21:1-3, 1996.
30. Boppart S A, Bouma B E, Pitris C, Tearney G J, Fujimoto J G. Forward-imaging instruments for optical coherence tomography. Opt. Lett. 22:1618-20, 1997.
31. Bouma B E, Tearney G J, Compton C C, Nishioka N S. High-resolution imaging of the human esophagus and stomach in vivo using optical coherence tomography. Gastrointest. Endosc. 51:467-74, 2000.
32. Sivak M V Jr, Kobayashi K, Izatt J A, Rollins A M, Ung-Runyawee R, Chak A, Wong R C, Isenberg G A, Willis J. High-resolution endoscopic imaging of the gastrointestinal tract using optical coherence tomography. Gastrointest. Endosc. 51:474-79, 2000.
33. Li X, Boppart S A, Van Dam J, Mashimo H, Mutinga M, Drexler W, Klein M, Pitris C, Krinsky M L, Brezinski M E, 33. Fujimoto J G. Optical coherence tomography: advanced technology for the endoscopic imaging of Barrett's esophagus. Endoscopy 32:921-30, 2000.

34. Boppart S A, Brezinski M E, Bouma B E, Tearney G J, Fujimoto J G. Investigation of developing embryonic morphology using optical coherence tomography. Dev. Biol. 177:54-63, 1996.

35. Boppart S A, Brezinski M E, Tearney G J, Bouma B E, Fujimoto J G. Imaging developing neural morphology using optical coherence tomography. J. Neurosci. Meth. 2112:65-72, 1996.

36. Boppart S A, Tearney G J, Bouma B E, Southern J F, Brezinski M E, Fujimoto J G. Noninvasive assessment of the developing *Xenopus* cardiovascular system using optical coherence tomography. Proc. Natl. Acad. Sci. USA 94:4256-61, 1997.

37. Boppart S A, Bouma B E, Pitris C, Southern J F, Brezinski M E, Fujimoto J G. In vivo cellular optical coherence tomography imaging. Nature Med. 4:861-64, 1998.

38. Pitris C, Goodman A K, Boppart S A, Libus J J, Fujimoto J G, Brezinski M E. High resolution imaging of gynecological neoplasms using optical coherence tomography. Obstet. Gynecol. 93:135-39, 1999.

39. Pitris C, Jesser C, Boppart S A, Stamper D, Brezinski M E, Fujimoto J G. Feasibility of optical coherence tomography for high resolution imaging of human gastrointestinal tract malignancies. J. Gastroenterol. 35:87-92, 1999.

40. Barton J K, Hoying J B, Sullivan C J. Use of microbubbles as an optical coherence tomography contrast agent, Contrast Material Research Conference, Woodstock, VT (published in supplement to "Academic Radiology," Sept. 12-17, 1999).

41. Licha, K. Contrast agents for optical imaging. Topics Curr. Chem. 222:1-29, 2002.

42. Lee T M, Oldenburg A L, Sitafalwalla S, Marks, D L, Luo W, Toublan F J J, Suslick K S, Boppart S A. Engineered microsphere contrast agents for optical coherence tomography. Opt. Lett., submitted (2003).

43. Vitkin A, Woolsey J, Wilson B C, Anderson R R. Optical and thermal characterization of natural (*sepia officinalis*) melanin. Photochem. Photobiol. 59:455-62, 1994.

44. Toublan F J J, Reynolds J J, Hartleben S H, Sitafalwalla S, Suslick K S, Boppart S A. Magnetically-inducible optical contrast agents for optical coherence tomography. Proc. Opt. Soc. Am. Biomed. Topical Mtg., Miami, Fla., 2002.

45. Sevick-Muraca E M, Houston J P, Gurfinkel, M. Fluorescence-enhanced, near infrared diagnostic imaging with contrast agents. Curr. Op. Chem. Biol. 6:642-50, 2002.

46. Zaheer A.; Lenkinski, R. E.; Mahmood, A.; Jones, A. G.; Cantley, L. C.; Frangioni, J. V. In vivo near-infrared fluorescence imaging of osteoblastic activity. Nature Biotechnol. 19:1148-54, 2001.

47. Jordan A, Scholz R, Wust P, Fahling H, Felix R. Magnetic fluid hyperthermia (MFH): Cancer treatment with AC magnetic field induced excitation of biocompatible superparamagnetic nanoparticles. J. Magn. Magn. Mater. 201:413-19, 1999.

48. Hiergeist, R., et al. Application of magnetite ferrofluids for hyperthermia. J. Magn. Magn. Mater. 201:420-22, 1999.

49. Jensen T, Kelly L, Lazarides A, Schatz G C. Electrodynamics of noble metallic nanoparticles and nanoparticle clusters. J. Cluster Sci. 10:295-317, 1999.

50. El-Sayed, M. A. Some interesting properties of metals confined in time and nanometer space of different shapes. Acc. Chem. Res. 34:257-64, 2001.

51. Hayat, M. A., ed. Colloidal Gold: Principles, Methods, and Applications, Volume 1 (San Diego: Wei and Boppart EB-03-003 27 Academic Press), 1989.

52. Reussell-Jones, G. J. Use of vitamin B-12 conjugates to deliver protein drugs by the oral route. Crit. Rev. Ther. Drug Carrier Sys. 15:557-86, 1998

53. Tuting, T. The immunology of cutaneous DNA immunization. Curr Op Mol Ther 1:216-25, 1999.

54. Harrington K J, Spitzweg C, Bateman A R, Morris J C, Vile R G. Gene therapy for prostate cancer: current status and future prospects. J. Urology 166:1220-33, 2001.

55. Shipway A N, Katz E, Willner I. Nanoparticle arrays on surfaces for electronic, optical, and sensor applications. ChemPhysChem 1:18-52, 2000.

56. Kreibig U, Vollmer M. Optical Properties of Metal Clusters. (New York, Springer), 1995.

57. Yguerabide J, Yguerabide E E. Light-scattering submicroscopic particles as highly fluorescent analogs and their use as tracer labels in clinical and biological applications. I. Theory. Anal Biochem. 262:137-56, 1998.

58. van der Zande B, Böhmer M R, Fokkink, L G J., Schönenberger, C. Colloidal dispersions of gold rods: synthesis and optical properties. Langmuir 16:451-58, 2000.

59. Yu Y Y, Chang S S, Lee C L., Wang C R C. Gold nanorods: electrochemical synthesis and optical properties. J Phys Chem. B 101:6661-64, 1997.

60. Jana N R, Gearheart L, Murphy C J. Wet chemical synthesis of high aspect ratio cylindrical gold nanorods. Ibid. 105:4065-67, 2001.

61. Cepak V M, Martin C R. Preparation and Stability of Template-Synthesized Metallic nanorod Sols in Organic Solvents. J. Phys. Chem. B 102:9985-90, 1998.

62. Nicewarner-Peña S R., et al. Submicrometer metallic barcodes. Science 294:137-41, 2001.

63. Mock J J, Oldenburg S J, Smith D R, Schultz D A, Schultz S. Complosite plasmon resonant nanowires. Nano. Lett. 2:465-69, 2002.

64. Novak J, Nickerson C, Franzen S, Feldheim, D L. Purification of molecularly bridged metallic nanoparticle arrays by centrifugation and size exclusion chromatography. Anal. Chem. 73:5758-61, 2001.

65. Masuda H., Fukada K. Ordered metallic nanohole arrays made by a two-step replication of honeycomb structures of anodic alumina. Science 268:1466-68, 1995.

66. Li A P, Muüller F, Birner A, Nielsch K, Gösele U. Polycrystalline nanopore arrays with hexagonal ordering on aluminum. J. Vac. Sci. Technol. A, 17:1428-31, 1999.

67. Nielsch K, Choi J, Schwirn K, Wehrspohn R B, Gösele U. Self-ordering regimes of porous alumina: the 10% porosity rule. Nano Lett. 2:677-80, 2002.

68. Li F., Zhang L, Metzger R M. On the growth of highly ordered pores in anodized aluminum oxide. Chem. Mater. 10:2570-80, 1998.

69. Sönnichsen C, Franzl T, Wilk T, von Plessen G, Feldmann J. Drastic reduction of plasmon damping in gold nanorods. Phys. Rev. Lett. 88:077402, 2002.

70. Kim F, Song J H, Yang P. Photochemical synthesis of gold nanorods. J. Am. Chem. Soc. 124:14316-17, 2002.

71. Jin R, Cao Y, Mirkin C A, Kelly K L, Schatz G C, Zheng J G. Photoinduced conversion of silver nanospheres to nanoprisms. Science 294:1901-03, 2001.

72. Mock J J, Baric M, Smith D R, Schultz D A, Schultz S J. Shape effects in plasmon resonance of individual colloidal silver nanoparticles. J. Chem. Phys. 116:6755-59, 2002.

73. Has A J, van Dune R P. A nanoscale optical biosensor: sensitivity and selectivity of an approach based on the local- 74. Handley D A, Arleen C M, White L D, Chine S. Colloidal gold-low density lipoprotein conjugates as membrane receptor probes. Proc. Natl. Acad. Sci. USA 78:368-71, 1981.

75. Handley D A. The development and application of colloidal gold as a microscopic probe. In Colloidal Gold: Principles, Methods, and Applications, M. A. Hayat, ed. (San Diego, Academic Press), pp. 13-32, 1989.

76. Handley D A, Chine S. Colloidal gold labeling studies related to vascular and endothelial function, hemostasis and receptor-mediated processing of plasma macromolecules. Eur. J. Cell. Biol. 43:163-74, 1987.

77. Kolb-Bachofen V, Schlepper-Schafer J, Vogell W, Kolb H. Electron microscopic evidence for an asialoglycoprotein receptor on Kupffer cells: localization of lectin-mediated endocytosis. Cell 29:859-66, 1982.

78. Kempka G, Kolb-Bachofen V. Binding, uptake, and transcytosis of ligands for mannose-specific receptors in rat liver: an electron microscopic study. Exp Cell Res 176, 38-48, 1988.

79. Van der Smissen P, Vael T, Courtoy P J, Baudhuin P. Ligand-induced clustering of asialoglycoprotein receptors on rat hepatocytes at 4° C. Eur. J. Cell. Biol. 60:122-30, 1993.

80. Van der Smissen P, Courtoy P J, Baudhuin P. Quantitative analysis of clustering on biological membranes: methodology and application to ligand-induced asialoglycoprotein receptor redistribution on rat hepatocytes. Eur. J. Cell. Biol. 69:45-54, 1996.

81. Tanaka K, Mitsushima A, Yamagata N, Kashima Y, Takayama H. Direct visualization of colloidal gold-bound molecules and a cell-surface receptor by ultrahigh-resolution scanning electron microscopy. J. Microsc. 161:455-61, 1991.

82. Templeton A C, Wuelfing M P, Murray R W. Monolayer protected cluster molecules. Acc. Chem. Res. 33:27-36, 2000.

83. Stavens K B, Pusztay S V, Zou S, Andres R P, Wei A. Encapsulation of Neutral Gold Nanoclusters by Resorcinarenes. Langmuir 15:8337-39, 1999.

84. Wei A, Stavens K B, Pusztay S V, Andres R P. Synthesis and Characterization of Resorcinarene-Encapsulated Nanoparticles. MRS Symp. Proc. Ser. 581:59-63, 1999.

85. Balasubramanian R, Xu J, Kim B, Sadtler B, Wei A. Extraction and dispersion of large gold nanoparticles in organic solvents. J. Dispers. Sci. Tech. 22:485-89, 2001.

86. Balasubramanian R, et al. Dispersion and stability studies of resorcinarene-encapsulated gold nanoparticles. Langmuir 18:3676-81, 2002.

87. Kim B, Tripp S L, Wei A. Self-Organization of Large Gold Nanoparticle Arrays. J. Am. Chem. Soc. 123:7955-56, 2001.

88. Liz-Marzan L M, Giersig M, Mulvaney P. Homogeneous silica coating of vitreophobic colloids. Chem. Commun. 731-32, 1996.

89. Ung T, Liz-Marzan L M, Mulvaney P. Controlled method for silica coating of silver colloids. Influence of coating on the rate of chemical reactions. Langmuir 14:3740-48, 1998.

90. Liu Q, Xu Z, Finch J A, Egerton R. A novel two-step silica-coating process for engineering magnetic nanoparticles. Chem. Mater. 10:3936-40, 1998.

91. Hardikar V V, Matijevic E. Coating of nanosize silver particles with silica. J. Colloid. Interf. Sci. 221:133-36, 2000.

92. Quaroni L, Chumanov G. Preparation of Polymer-Coated Functionalized Silver Nanoparticles. J. Am. Chem. Soc. 121:10642-43, 1999.

93. Clark H A, Campagnola P J, Wuskell J P, Lewis A, Loew L M. Second harmonic generation properties of fluorescent polymer-encapsulated gold nanoparticles. J. Am. Chem. Soc. 122:10234-25, 2000.

94. Wei A, Kim B, Pusztay S V, Tripp S L, Balasubramanian R. Resorcinarene-encapsulated nanoparticles: building blocks for self-assembled nanoparticles. J. Inclusion Phenom. Macrocyclic Chem. 41, in press (2001).

95. Sadtler B, Wei A. Spherical ensembles of gold nanoparticles on silica: electrostatic and size effects. Chem. Commun., 1604-05, 2002.

96. Tripp S L, Pusztay S V, Ribbe A E, Wei A. Self-assembly of cobalt nanoparticle rings. J. Am. Chem. Soc. 124:7914-15, 2002.

97. Timmerman P, Verboom W, Reinhoudt D N. Resorcinarenes. Tetrahedron 52:2663-704, 1996.

98. Stavens K B, Pusztay S V, Zou S, Andres R P, Wei A. Encapsulation of Neutral Gold Nanoclusters by Resorcinarenes. Langmuir 15:8337-39, 1999.

99. Toth C A, Cain C P, Stein C D. et al. Retinal effects of ultrashort laser pulses in the rabbit eye. Invest. Opthalmol. Vis. Sci. 36:1910, 1995.

100. Cain C P, Toth C A, Noojin G D, Carothers V, Stolarski D J, Rockwell B A. Thresholds for Visible Lesions in the Primate Eye Produced by Ultrashort Near-Infrared Laser Pulses. Invest. Opthalmol. Vis. Sci., 40:2343-49, 1999.

101. Boppart S A, Herrmann J, Pitris C, Stamper D L, Brezinksi M E, Fujimoto J G. High-Resolution Optical Coherence Tomography-Guided Laser Ablation of Surgical Tissue. J. Surg. Res., 82:275-84, 1999.

102. Schmitt J M, Knuttel A, Yadlowsky M, Eckhaus A A. Optical coherence tomography of a dense tissue: statistics of attenuation and backscattering. Phys. Med. Biol. 39:1705-20, 1994.

103. Lin S P, Wang L, Jacques S L, Tittel F K. Measurement of tissue optical properties by the use of oblique-incidence optical fiber reflectometry. Appl. Opt. 36:136-43, 1997.

104. Ivin K J, Mol J C. Olefin Metathesis and Metathesis Polymerization, 2nd ed. (San Diego, Academic Press), 1997.

105. Lee R J, Low P S. Delivery of Liposomes to Cultured KB Cells via Folate Receptor-Mediated Endocytosis. J. Biol. Chem. 269:3198-204, 1994.

106. Grubbs R H, Miller S J, Fu G C. Ring-Closing Metathesis and Related Processes in Organic Synthesis. Acc. Chem. Res. 28:446-52, 1995.

107. Blackwell H E, O'Leary D J, Chatterjee A K, Washenfelder R A, Bussmann D A, Grubbs R H. New approaches to olefin cross-metathesis. J. Am. Chem. Soc. 122:58-71, 2000.

108. Slaga T J, Gimenez-Conti I B. An animal model for oral cancer. J. Natl. Cancer Inst. Monogr. 13:55-60, 1992.

109. Pusztay S V, Wei A, Stavens K B, Andres R P. Encagement of Gold Nanoclusters in Crosslinked Resorcinarene Shells. Supramol. Chem. 14:289-92, 2002.

110. Gimenez-Conti I B, Slaga T J. The hamster cheek pouch carcinogenesis model. J. Cell. Biochem. 17F:83-90, 1993.

111. Pathak I, Davis N L, Hsiang Y N, Quenville N F, Palcic B. Detection of squamous neoplasia by fluorescence imaging comparing porfimer sodium fluorescence to tissue autofluorescence in the hamster cheek pouch model. Am. J. Surg. 170:423-426, 1995.

112. Jackson J B. Halas N J. Silver Nanoshells: Variations in Morphologies and optical properties. J. Phys. Chem. B 105:2743-46, 2001.

113. Freeman R G, Grabar K C, Allison K J, Bright R M, Davis J A, Guthrie A P, Hommer M B, Jackson M A, Smith P C, Walter D G, Natan M J. Science 267:1629-1631, 1995.

114. Turkevich J, Stevenson P C, Hillier J. Discuss. Faraday Soc. 11:55-75, 1951

The invention claimed is:

1. A method of forming an image by optical coherence tomography, comprising:
   forming an image of a mixture by exposing the mixture to electromagnetic radiation; wherein the mixture comprises a patient and plasmon-resonant nanoparticles, wherein the electromagnetic radiation is provided to the mixture using optical coherence tomography in the frequency range of infra-red to ultraviolet light, and wherein the plasmon-resonant nanoparticles are anisotropic metallic nanoparticles having an extinction coefficient of at least $10^6 M^{-1} cm^{-1}$ at a frequency in the range of $10^{12}$ to $10^{17}$ Hz, wherein the anisotropic metallic nanoparticles comprise a magnetic metal, and wherein the magnetic metal is selected from nickel, cobalt, iron, and combinations thereof.

2. The method of claim 1, wherein the anisotropic metallic nanoparticles comprise nanorods or nanotriangles.

3. The method of claim 1, wherein the an isotropic metallic nanoparticles comprise gold.

4. The method of claim 1, wherein the anisotropic metallic nanoparticles further comprise a surface modification.

5. The method of claim 4, wherein the surface modification comprises a cross-linked surfactant shell.

6. The method of claim 5, wherein the cross-linked surfactant shell comprises at least one member selected from the group consisting of cross-linked resorcinarenes and cross-linked olefin.

7. The method of claim 6, further comprising, attached to the cross-linked surfactant shell, at least one member selected from the group consisting of folate, a monoclonal antibody, and a membrane receptor ligand.

8. The method of claim 1, further comprising exposing the mixture to magnetic field.

9. The method of claim 1, further comprising exposing the mixture to an electric field.

10. The method of claim 1, wherein the patient is a human patient.

11. A method of forming an image by optical coherence tomography, comprising:
    administering to a patient, anisotropic metallic nanoparticles having an extinction coefficient of at least $10^6 M^{-1} cm^{-1}$ at a frequency in the range of $10^{12}$ to $10^{17}$ Hz;
    wherein the anisotropic metallic nanoparticles are gold nanorods with a magnetic tip, and wherein the magnetic tip is one metal selected from the group consisting of cobalt, nickel, and iron;
    exposing the patient to electromagnetic radiation;
    collecting reflected electromagnetic radiation; and
    forming an enhanced contrast image from the collected electromagnetic radiation.

12. The method of claim 11, wherein the gold nanorods have an aspect ratio of 4:1 to 10:1 and a diameter of 10 nm to 100 nm.

13. The method of claim 11, wherein the patient is a human.

* * * * *

UNITED STATES PATENT AND TRADEMARK OFFICE
CERTIFICATE OF CORRECTION

PATENT NO. : 7,610,074 B2 Page 1 of 1
APPLICATION NO. : 10/753972
DATED : October 27, 2009
INVENTOR(S) : Stephen A. Boppart and Alexander Wei It is certified that error appears in the above-identified patent and that said Letters Patent is hereby corrected as shown below:

In the claims:

Col. 24, line 10, please insert --a-- between "to" and "magnetic".
Col. 24, line 19, please delete "$_1cm^{-1}$" and insert --$^1cm^{-1}$--.

Signed and Sealed this

Twenty-third Day of March, 2010

David J. Kappos
*Director of the United States Patent and Trademark Office*